US012109015B1

(12) United States Patent
Kiran et al.

(10) Patent No.: US 12,109,015 B1
(45) Date of Patent: Oct. 8, 2024

(54) APPARATUS AND METHOD FOR MONITORING PERFORMANCE OF A PHYSICAL ACTIVITY

(71) Applicant: Iterate Labs Inc., Ithaca, NY (US)

(72) Inventors: Apoorva Kiran, Boston, MA (US); Jesper T. Kristensen, New York, NY (US); Jason D. Guss, Boston, MA (US)

( * ) Notice: Subject to any disclaimer, the term of this patent is extended or adjusted under 35 U.S.C. 154(b) by 573 days.

(21) Appl. No.: 17/246,130

(22) Filed: Apr. 30, 2021

Related U.S. Application Data

(60) Provisional application No. 63/018,074, filed on Apr. 30, 2020.

(51) Int. Cl.
| | |
|---|---|
| G08B 23/00 | (2006.01) |
| A61B 5/00 | (2006.01) |
| A61B 5/11 | (2006.01) |
| A61B 5/22 | (2006.01) |
| A61B 5/389 | (2021.01) |
| G06Q 10/0639 | (2023.01) |

(52) U.S. Cl.
CPC .......... *A61B 5/1118* (2013.01); *A61B 5/0002* (2013.01); *A61B 5/1121* (2013.01); *A61B 5/22* (2013.01); *A61B 5/389* (2021.01); *A61B 5/746* (2013.01); *G06Q 10/06398* (2013.01); *A61B 2503/20* (2013.01); *A61B 2562/0219* (2013.01); *A61B 2562/0223* (2013.01); *A61B 2562/0271* (2013.01)

(58) Field of Classification Search
CPC ... A61B 5/1118; A61B 5/0002; A61B 5/1121; A61B 5/22; A61B 5/389; A61B 5/746; A61B 2503/20; A61B 2562/0219; A61B 2562/0223; A61B 2562/0271; G06Q 10/06398
See application file for complete search history.

(56) References Cited

U.S. PATENT DOCUMENTS

| | | | | |
|---|---|---|---|---|
| 7,503,878 | B1 * | 3/2009 | Amsbury | A61B 5/1122 482/3 |
| 8,036,842 | B2 * | 10/2011 | DeVaul | A61B 5/7264 702/79 |
| 10,234,934 | B2 | 3/2019 | Connor | |
| 10,492,724 | B2 * | 12/2019 | Beamer | A61B 5/6802 |
| 10,568,550 | B2 | 2/2020 | Ronchi et al. | |

(Continued)

FOREIGN PATENT DOCUMENTS

| | | |
|---|---|---|
| WO | WO2014071460 A1 | 5/2014 |
| WO | WO2014169329 A1 | 10/2014 |

(Continued)

*Primary Examiner* — Toan N Pham
(74) *Attorney, Agent, or Firm* — Sunstein LLP

(57) ABSTRACT

A device monitors performance by a subject of a physical activity. The device includes first and second assemblies that each includes a housing, a set of sensors, and a communication link to the other one of the assemblies. Each assembly is configured for removable attachment to corresponding body parts of the subject that have relative motion about a joint of the subject. The device has a resilient physical link that couples the assemblies and allows relative motion of the assemblies. The device further includes a controller disposed in the device for processing data from the sensors, memory for storing the data, and a wireless transceiver disposed in the system for transmitting the data to a destination.

17 Claims, 50 Drawing Sheets

(56) References Cited

U.S. PATENT DOCUMENTS

| | | | |
|---|---|---|---|
| 10,674,965 | B2 | 6/2020 | Elhawary |
| 10,772,538 | B1 | 9/2020 | Elhawary et al. |
| 10,869,632 | B2 | 12/2020 | De Pardo et al. |
| 11,064,936 | B2 * | 7/2021 | D'Lima .................. A61B 5/11 |
| 11,172,874 | B2 * | 11/2021 | Obma .................. A61B 5/6898 |
| 11,328,239 | B2 | 5/2022 | Baek et al. |
| 2007/0250286 | A1 | 10/2007 | Duncan et al. |
| 2014/0032124 | A1 | 1/2014 | Umer et al. |
| 2015/0045700 | A1 * | 2/2015 | Cavanagh ............. G16H 40/67 600/595 |
| 2016/0242646 | A1 * | 8/2016 | Obma ...................... A61B 5/01 |
| 2017/0296129 | A1 | 10/2017 | Petterson et al. |
| 2017/0344919 | A1 | 11/2017 | Chang et al. |
| 2019/0167988 | A1 * | 6/2019 | Shahriari ............. A61N 1/3603 |
| 2020/0174517 | A1 | 6/2020 | Martinez et al. |

FOREIGN PATENT DOCUMENTS

| | | |
|---|---|---|
| WO | WO2015039176 A1 | 3/2015 |
| WO | WO2019051564 A1 | 3/2019 |
| WO | WO2021/257546 A1 | 12/2021 |
| WO | WO2022/087029 A1 | 4/2022 |

\* cited by examiner

SECTION C-C

FIG. 3 SCALE 1 : 1

Structured Worker Motion Data — 1406

| timestamp (t) | delta acceleration (a) | magnetic field (m) |
|---|---|---|
| 1000 | -1.2 | 4.1 |
| 1001 | 0.6 | 8 |
| 1002 | 0.4 | 4 |
| 1003 | 1 | 7 |
| ... | ... | ... |

Fig. 15

Ergonomic Scores

FIG. 27

2900 2902 Top 10 at-risk jobs by average safety score

| Name of Job | Average Safety Score | Average Strain Score | Average Posture Score | Average Speed Score |
|---|---|---|---|---|
| Membrane Skinner | 6.9 | 7 | 2 | 5 |
| Debone | 6.7 | 5 | 5 | 5 |
| Washing | 2.1 | 2.4 | 4.2 | 1 |
| Cleaning | 3.4 | 1.2 | 4.1 | 5 |
| Cutting | 6 | 7 | 3.8 | 6 |
| Sorting | 0.8 | 1.1 | 2 | 3.8 |
| Station 1 | 6.7 | 5 | 5 | 5 |
| Deloin | 2.1 | 2.4 | 2.1 | 1.2 |
| Station 2 | 3.4 | 1.2 | 4.1 | 5 |
| Blade | 6 | 7 | 4.4 | 6 |

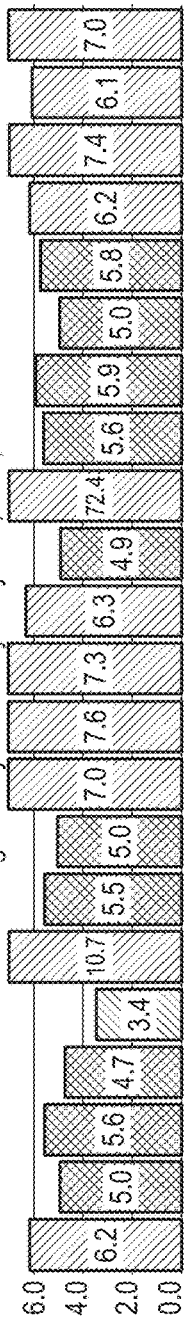
FIG. 32

APPARATUS AND METHOD FOR MONITORING PERFORMANCE OF A PHYSICAL ACTIVITY

PRIORITY

The present application claims the benefit of U.S. provisional application Ser. No. 63/018,074, filed Apr. 30, 2020, which is hereby incorporated herein by reference in its entirety.

TECHNICAL FIELD

The present invention relates to systems that monitor performance of a physical activity using wearable devices.

BACKGROUND ART

The human, as well as non-human, such as robots, animals etc., rely on complex body motions to perform various physical tasks. To be able to perform a task in an optimal way, it is important to measure, refine, and optimize these body motions. For example, in an industrial setting, workers are often unaware if they are using improper motions for performing physical activities, which can be potentially inefficient, counterproductive, or cause musculoskeletal injuries, such as repetitive motion injuries. An improper motion performed by workers can cause injuries if the motion performed by them is ergonomically unsafe. The loss of productivity and work quality can be also be attributed to spatially suboptimal motion.

SUMMARY OF THE EMBODIMENTS

In accordance with one embodiment of the invention, a device for monitoring performance by a subject of a physical activity. The device a first and second assemblies, each assembly including a housing and a set of sensors and a communication link to the other one of the assemblies and configured for removable attachment to corresponding body parts of the subject. The body parts have relative motion about a joint of the subject, the assemblies constituting a system. The device also includes a controller disposed in the system for processing data from the sensors. The device further includes a wireless transceiver disposed in the system for transmitting the processed data to a destination. The device also includes a resilient physical link coupling the two assemblies and allowing relative motion of the two assemblies.

In another related embodiment, the device further includes memory for storing the data. In further related embodiments, the device includes a battery for powering the device. In another related embodiment, the device includes a charging module for charging the battery.

Optionally, the resilient physical link includes a communication bus. Optionally, the set of sensors are selected from the grouping consisting of an accelerometer, a gyroscope, a magnetometer, a thermistor, an EMG sensor, and combinations thereof. Optionally, the wireless transceiver transmits data from the sensors to a server and the server processes the data and generates reports and alerts.

In a related embodiment, processing the data includes cleaning the data. Optionally, the data is cleaned using a technique selected from the group consisting of clustering, principal component analysis (PCA), mean mesh (MM) PCA, data imputation, time stabilization, standard deviation of time, temporal-angular filter, and combinations thereof.

In another related embodiment, processing the data includes performing analytics to the data. Optionally, performing the analytics includes computing ergonomic metrics based on the data. Alternatively or in addition, the ergonomic metrics are selected from the group consisting of strain, posture, speed, differential angle, and combinations thereof. Alternatively or in addition, performing the analytics includes scoring each ergonomic metrics. Alternatively or in addition, the scoring is based on the radial angle, ulnar angle, flexion angle, extension angle, pronation angle, supination angle, and combinations thereof of the relative motion. Alternatively or in addition, the scoring is calculated using an assessment method selected from the group consisting of RULA scores, Moore Garg Strain Index, American Conference of Governmental Industrial Hygienists (ACGIH) Hand Activity Level, Assessment of Repetitive Task (ART), Iterate Lab scores. Alternatively or in addition, the scoring is based on intensity, duty cycle, and frequency of the relative motion exceeding a pre-defined safe limit. Alternatively or in addition, performing the analytics includes employing machine learning techniques to assess data associated with repetitive physical tasks performed by the subject.

Optionally, processing the data includes generating a report based on the data and transmitting the report to a computing device of a user. Optionally, processing the data includes generating an alert based on the data and transmitting the alert to a computing device of the user.

Optionally, performing the analytics includes determining parameters applicable to performing tasks associated with a lean manufacturing methodology, the methodology selected from the group consisting of standard work, labor standards, and combinations thereof, such parameters selected from the group consisting of cycle time, cycle count, uptime-to-downtime ratio, compliance, and combinations thereof.

BRIEF DESCRIPTION OF THE DRAWINGS

The foregoing features of embodiments will be more readily understood by reference to the following detailed description, taken with reference to the accompanying drawings, in which:

FIG. 15 is a table illustrating structured worker motion data, in accordance with an embodiment of the present invention;

FIG. 27 shows the rapid upper limb assessment (RULA) method used to calculate an ergonomic score, in accordance with prior art.

FIGS. 29-30 provide exemplary types of reports generated by the analytics platform of FIG. 13, in accordance with an embodiment of the present invention;

FIGS. 31-32 show example reports provided, by the analytics platform of FIG. 13, to a mobile computing device of a subject on the subject's monitored performance, in accordance with an embodiment of the present invention.

DETAILED DESCRIPTION OF SPECIFIC EMBODIMENTS

Figure 1:
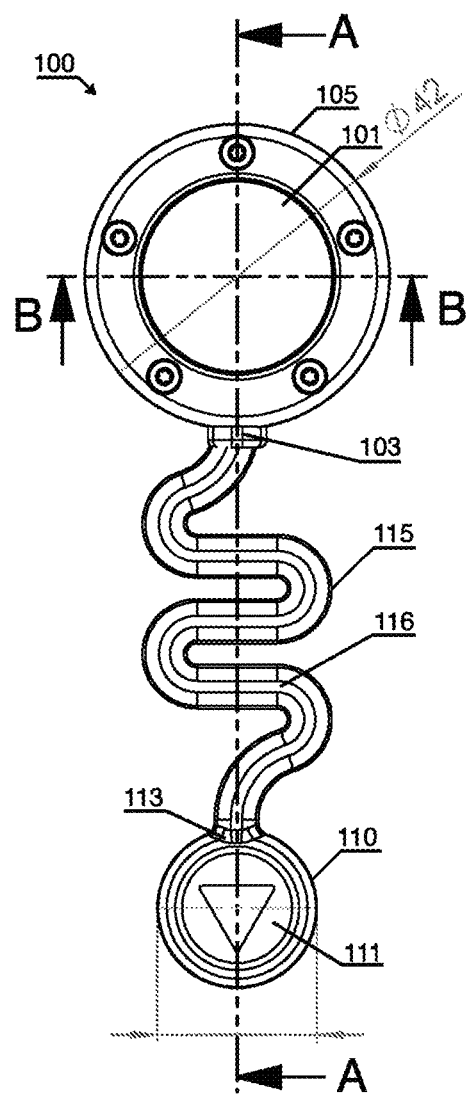
FIG. 1 is a top view of a wearable device for monitoring a subject's performance of a physical activity, in accordance with an embodiment of the present invention.

Definitions. As used in this description and the accompanying claims, the following terms shall have the meanings indicated, unless the context otherwise requires:

A "subject" includes a human, a mammal, a non-mammalian vertebrate, and a robot.

A "communication link" between assemblies includes a physical communication bus and a wireless communication facility.

A "set" includes at least one member.

A "computer process" is the performance of a described function in a computer system using computer hardware (such as a processor, field-programmable gate array or other electronic combinatorial logic, or similar device), which may be operating under control of software or firmware or a combination of any of these or operating outside control of any of the foregoing. All or part of the described function may be performed by active or passive electronic components, such as transistors or resistors. In using the term "computer process" we do not necessarily require a schedulable entity, or operation of a computer program or a part thereof, although, in some embodiments, a computer process may be implemented by such a schedulable entity, or operation of a computer program or a part thereof. Furthermore, unless the context otherwise requires, a "process" may be implemented using more than one processor or more than one (single- or multi-processor) computer.

A "network-enabled performance monitoring device" is a device, wearable by a subject, configured to transmit, over a network, data characterizing physical performance of the subject in carrying out a work task.

A "work task" is a task pertinent to a member selected from the group consisting of manufacturing of goods, shipping of goods, distribution of goods, performing of non-entertainment services requiring physical activity, and combinations of the foregoing.

Embodiments of the present invention monitor the performance of physical activities by a subject to determine the subject's use of improper ergonomic motions and motions that lead to suboptimal performance. Some embodiments include a wearable device having sensors that capture data on the subject's motions during performance of a physical activity. In some embodiments, the wearable device stores and analyzes the data to notify the subject of the use of such improper ergonomic motions as well as motions that are unproductive and suboptimal. In some embodiments, the wearable device reports the data, via a gateway, to a server that aggregates, cleans, structures, and analyzes the data based on ergonomic metrics (e.g., strain, differential angle, etc.). In some embodiments, the analysis includes the employment of machine learning techniques to assess data associated with repetitive physical tasks performed by the subject. In some embodiments, the server calculates a safety score for each of the ergonomic metrics based on an ergonomic assessment method, such as RULA. In some embodiments, the server provides results of the analysis to the computing device of the subject and other interested individuals (e.g., the subject's supervisor) in the form of visual reports and alerts. In some embodiments, the microprocessor onboard the device itself calculates the productivity score using the collected worker motion data stored in memory on the device itself. As opposed to this, in other embodiments, the device, or the server or a combination of the two computes the location of workers wearing the device. The analysis may be used for, but not limited to: 1) understanding worker motion associated with both untrained and trained workers to accelerate and optimize a training process; 2) assessing and improving the ergonomic safety of a job or individual worker; 3) assessing the productivity of a worker or group of workers by understanding individual cycle time, work quality, and collective process imbalances and interruptions; 4) mapping out the motions performed by a worker to minimize wasted motion and optimize a work task or workstation to a worker; 5) understanding a work process and individual subtasks of the process to optimize workflow, confirm tasks performed, and confirm the quality of tasks performed; 6) optimizing job rotations and breaks based upon worker motion performance and speed; 7) improving worker engagement by using worker motion data for gamification and for use of performance based incentive programs.

FIG. 1 is a top view of a wearable device for monitoring a subject's performance of a physical activity, in accordance with an embodiment of the present invention. The wearable device 100 is attachable to the subject at body parts having relative motion about a joint. The attached wearable device 100 measures and records the relative motion around the joint as motion data. For example, in the embodiment of FIG. 7, the wearable device 100 is attachable to the subject's hand and wrist to measure and record relative motion about the subject's wrist joint.

The wearable device 100 includes a first assembly 105 attachable to a first body part (e.g., hand) of the subject, a second assembly 110 attachable to a second body part (e.g., wrist) of the subject, and a resilient physical link 115 coupling the two assemblies 105, 110, such that the device 100 is mounted across the subject's joint (e.g., wrist joint) situated between the first and second body part. The resilient physical link 115 allows relative motion of the two assemblies 105, 110 about the joint of the subject.

As shown in FIG. 1, the first assembly 105 includes a housing 101 and a communication link 103 to the second assembly 110, and the second assembly 110 includes a housing 111 and a communication link 113 to the first assembly 105. As also shown in FIG. 1, the resilient physical link 115 of this embodiment includes a communication bus 116, coupled to the communication link 103 of the first assembly 105 and the communication link 113 of the second assembly 110, that communicates motion data between the first and second assemblies 105, 110. In other embodiments, the communication links 103, 113 are configured to wirelessly communicate motion data between the first and second assemblies 105, 110.

Figure 2:
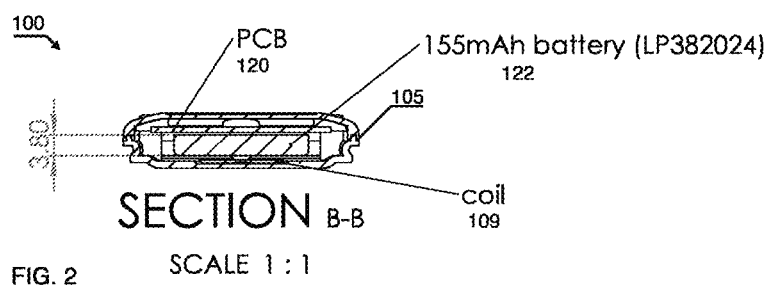
FIG. 2 is a cross sectional view of the device of FIG. 1, wherein the section is taken through the top and extends the width of the device.

FIG. 2 is a cross sectional view of the device of FIG. 1, wherein the section is taken through the top and extends the width of the device. FIG. 2 shows that the first assembly 105 includes a battery 122 (e.g., 155 mAh battery) that provides power to the device 100, and a printed circuit board (PCB) 120 that houses a microcontroller 132 (see FIG. 5) for processing the sensor data and a memory unit 134 (also FIG.

5) for storing the sensor data. FIG. 2 also shows that the first assembly 105 includes a coil 109 connecting the battery 122 to the PCB 120.

Figure 3:
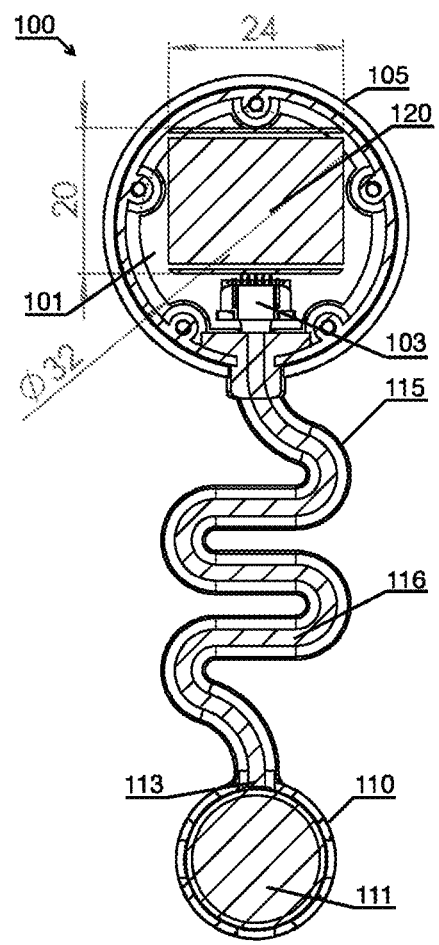
FIG. 3 is a longitudinal section of the device of FIG. 1, wherein the faces of the upper and lower portions of the device are oriented in a direction parallel to the page.

FIG. 3 is a longitudinal section of the device of FIG. 1, wherein the faces of the upper and lower portions of the device are oriented in a direction parallel to the page. FIG. 3 shows the connection of the PCB 120 to the communication link 103 in the first assembly 105 of the device.

Figure 4:
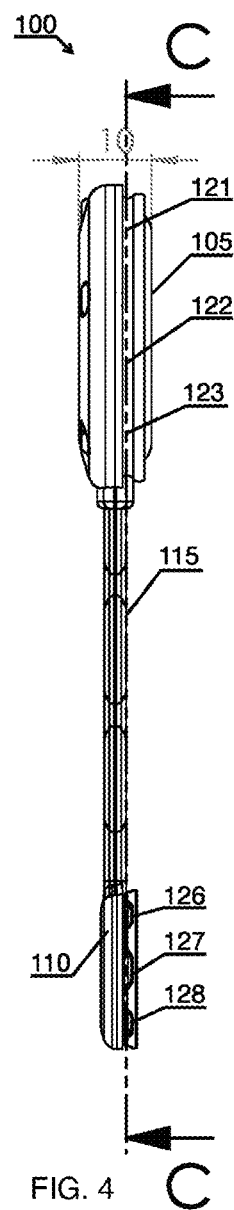
FIG. 4 is a bottom view of a longitudinal section of the device of FIG. 1, wherein the faces of the upper and lower portions of the right side of the device are oriented at right angles to the page.

FIG. 4 is a bottom view of a longitudinal section of the device of FIG. 1, wherein the faces of the upper and lower portions of the right side of the device are oriented at right angles to the page. FIG. 4 shows sensors 121, 122, 123 arranged in the first assembly 105 and sensors 126, 127, 128 arranged in the second assembly 110. These sensors 121, 122, 123, 126, 127, 128 measure motion about the subject's joint situated between the subject's first body part attached to the first assembly 105 and the subject's second body attached to the second assembly 110.

Figure 38A:
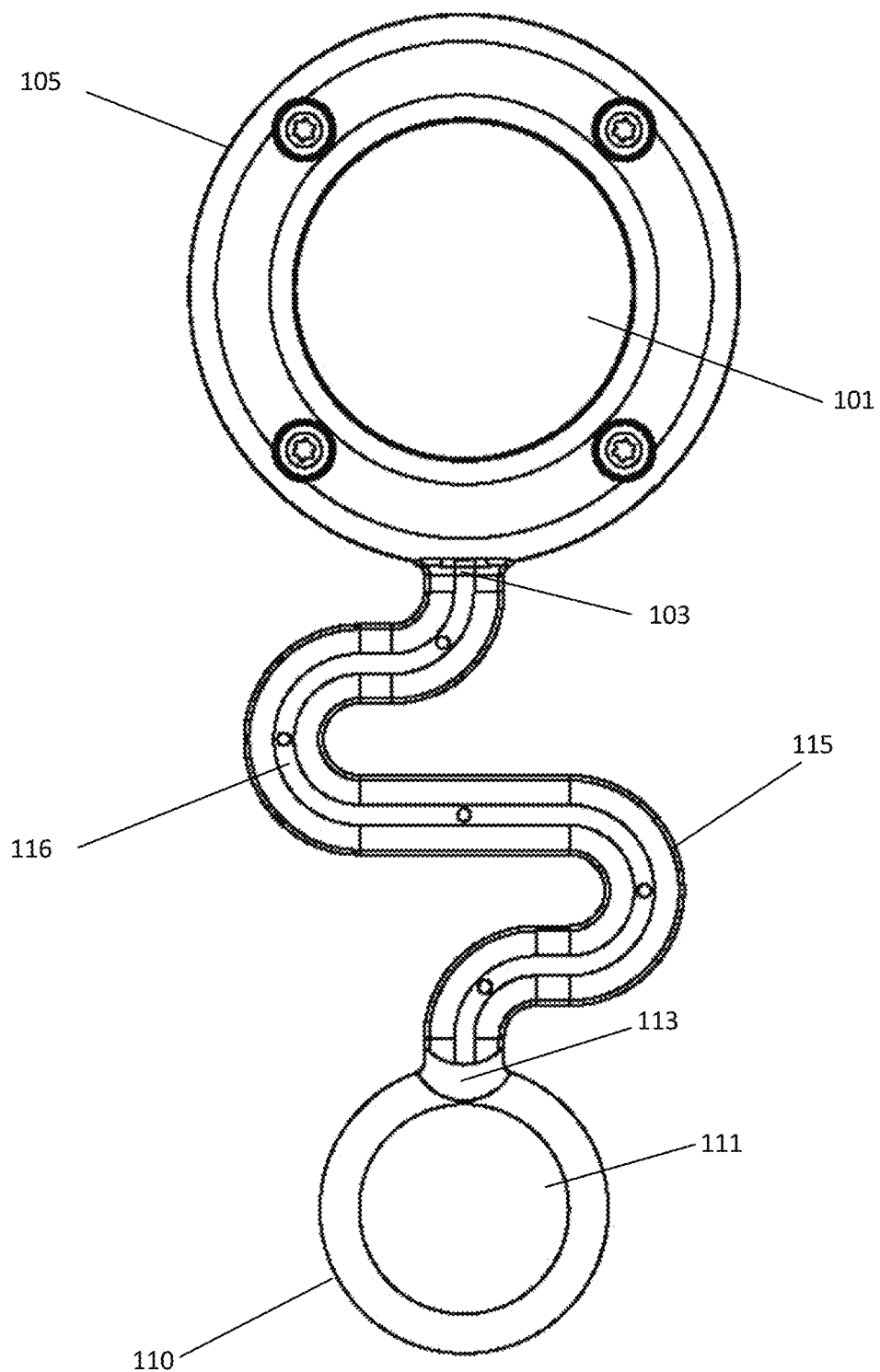
FIG. 38A shows a top view of a wearable device for monitoring a subject's performance of a physical activity, in accordance with an embodiment of the present invention.
Figure 38B:
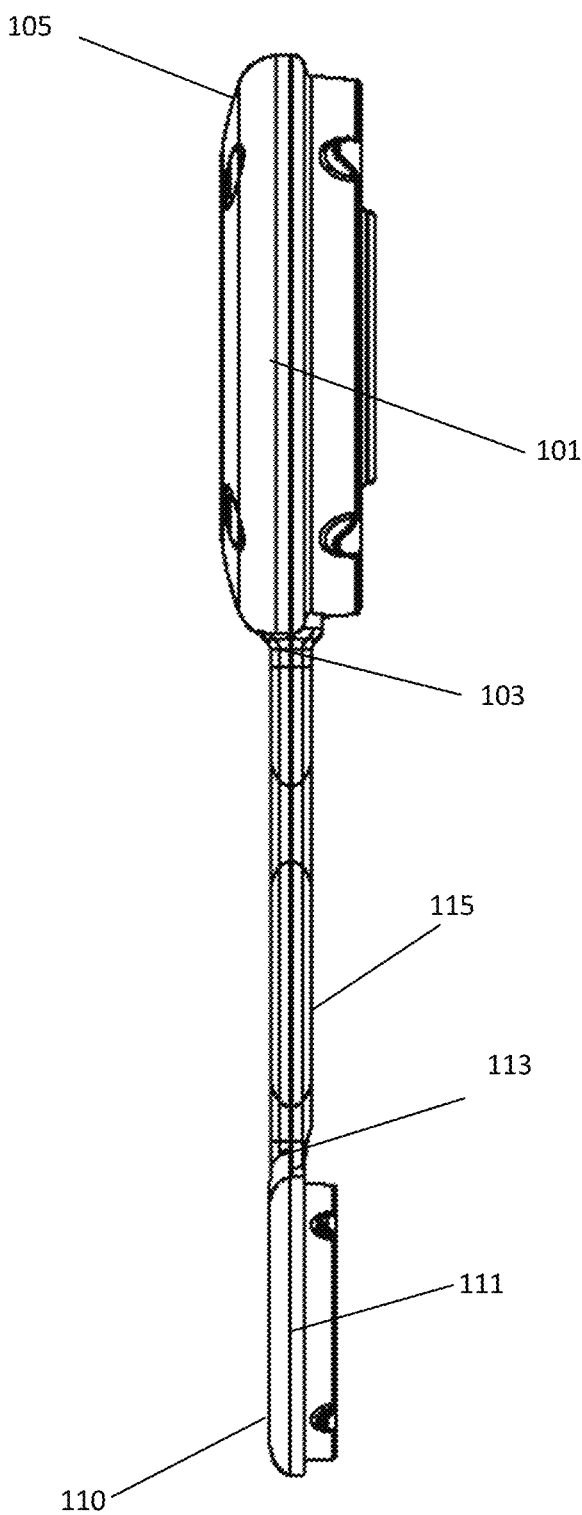
FIG. 38B shows a side view of a wearable device for monitoring a subject's performance of a physical activity, in accordance with an embodiment of the present invention.
Figure 38C:
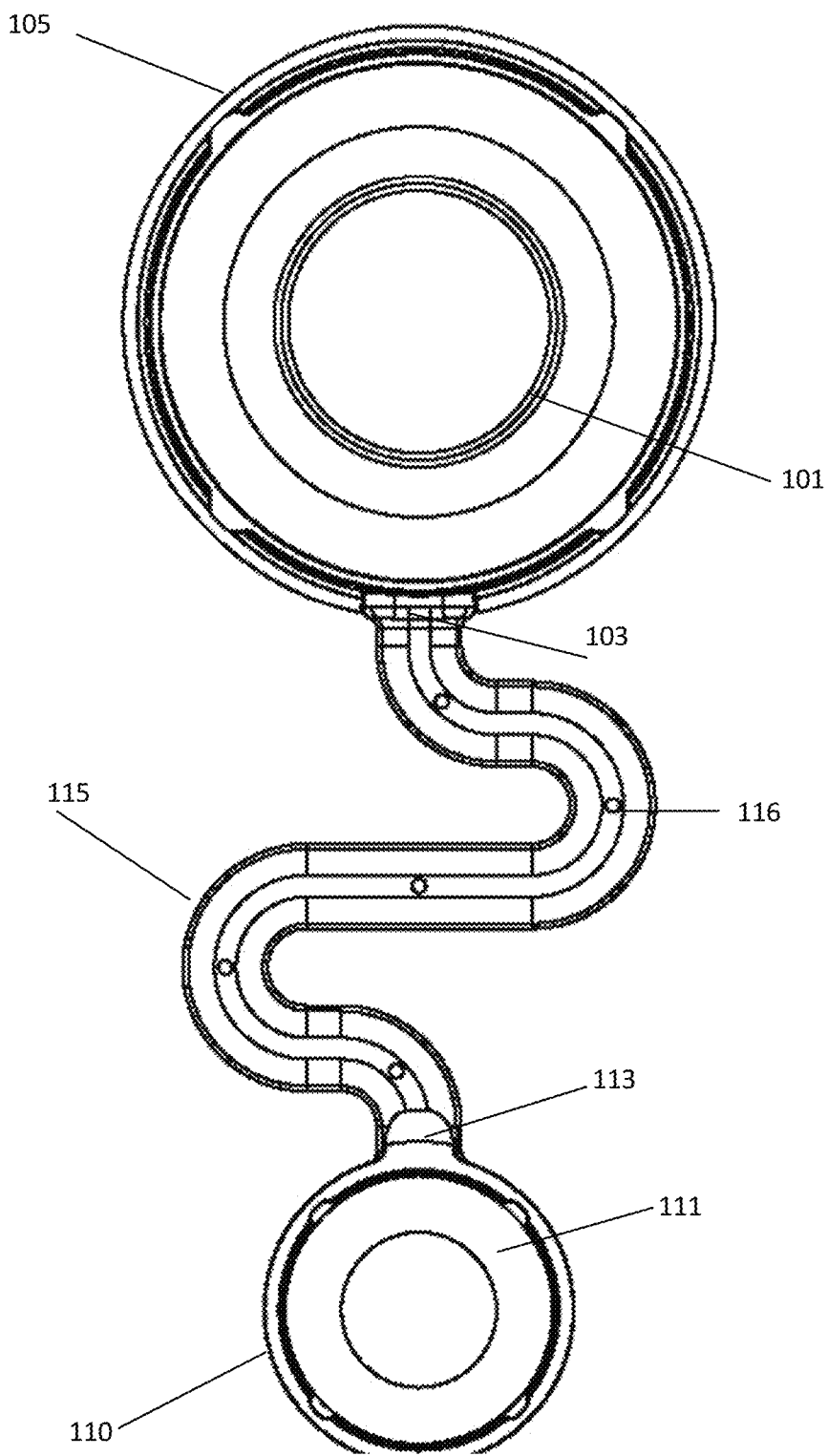
FIG. 38C shows a bottom view of a wearable device for monitoring a subject's performance of a physical activity, in accordance with an embodiment of the present invention.
Figure 38D:
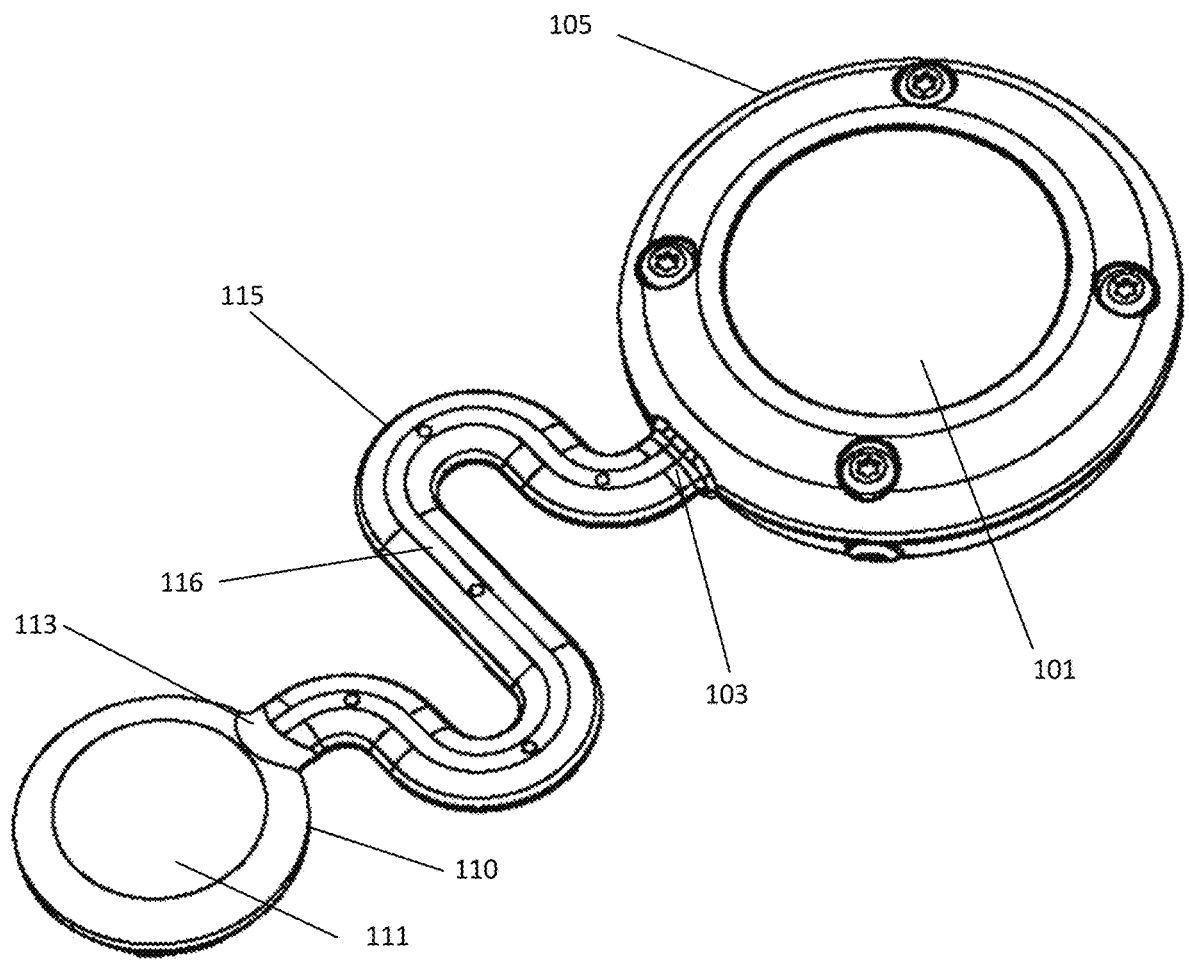
FIG. 38D shows an isometric view of a wearable device for monitoring a subject's performance of a physical activity, in accordance with an embodiment of the present invention.

FIGS. 38A, 38B, 38C, and 38D show a wearable device for monitoring a subject's performance of a physical activity, in accordance with an embodiment of the invention. The device having a first assembly 105 and a second assembly 110. FIG. 38A shows a top down view of the assemblies, FIG. 38B shows a side view of the assemblies, FIG. 38C shows a bottom view of the assemblies, and FIG. 38D shows an isometric view of the assemblies. A resilient link 115 may connect the two assemblies 105, 110. The first assembly includes a housing 101 and the second assembly includes a housing 111. The resilient physical link 115 may include a communication link 103 of the first assembly and a communication link 113 of the second assembly. A communication bus 116 may be coupled to the communication links 103, 113. The communication bus may communicate date between the first and second assemblies 105, 110. Alternatively, the communication links 103, 113 may communicate wirelessly with each other or with another device such as a server or database.

Figure 39A:
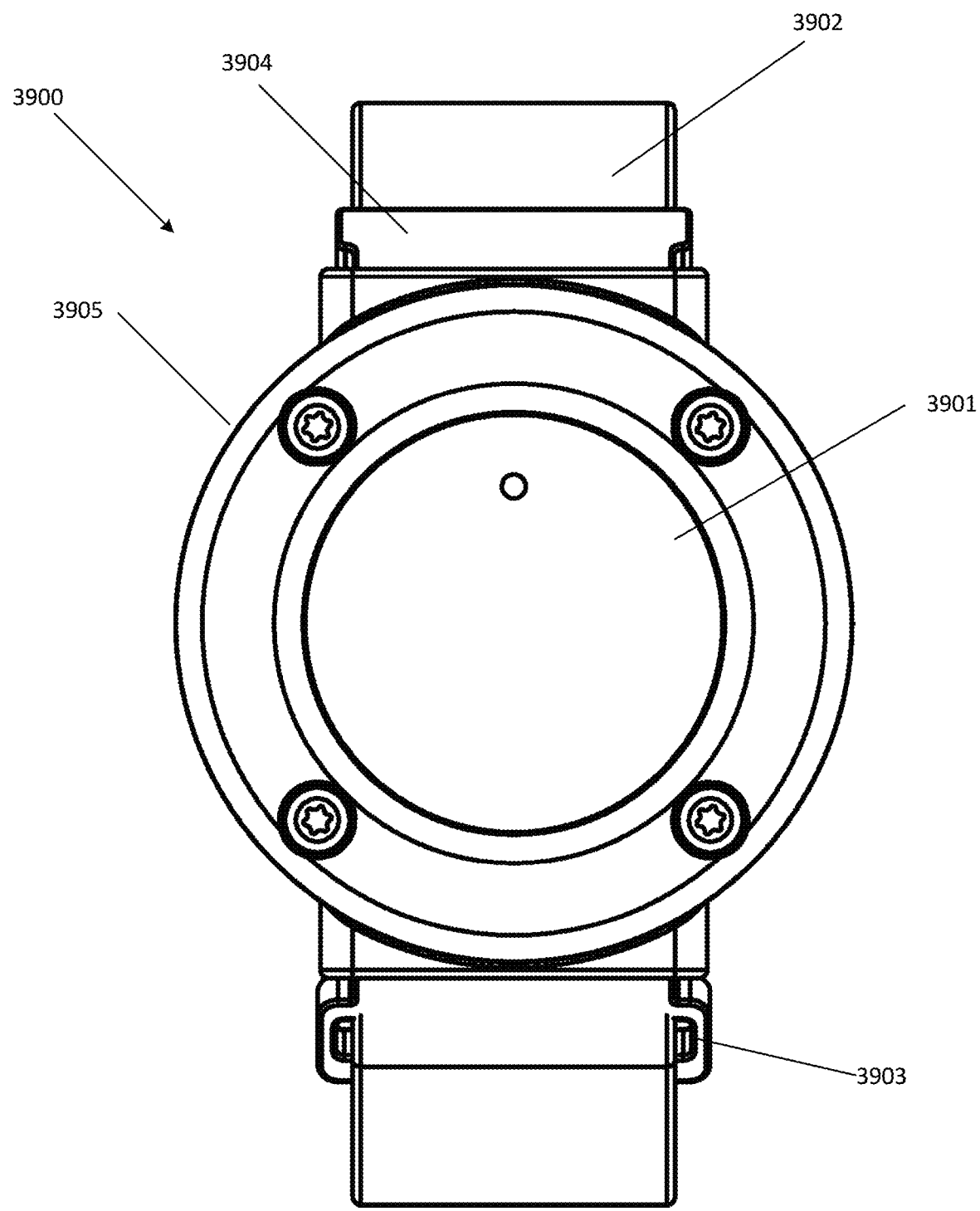
FIG. 39A shows a top view of a wearable device for monitoring a subject's performance of a physical activity, in accordance with an embodiment of the present invention.

FIG. 39A shows a top view of a wearable device for monitoring a subject's performance of a physical activity, such as a physical activity done during a work task, in accordance with an embodiment of the invention. The device has an assembly 3905 and a housing 3901. The housing 3901 may house architecture needed for data collection, data transmission, or data receiving, batteries, circuitry or other objects. The assembly 3905 is connected by at least one coupler 3903. In some embodiments a second coupler 3904 may be used. The couplers 3903, 3904 may connect the assembly 3905 to a strap 3902. The strap may be configured to secure the wearable device 3900 to a subject. In some embodiments the strap 3904 may be designed to secure the device 3900 to the subject's wrist. In some embodiments at least one coupler 3903 may allow for an adjustment of the length of strap 3902. The remaining length of strap 3902 would be slack. In some embodiments the strap 3902 may be elastic and not require adjustment to secure the device 3900 to the subject.

Figure 39B:
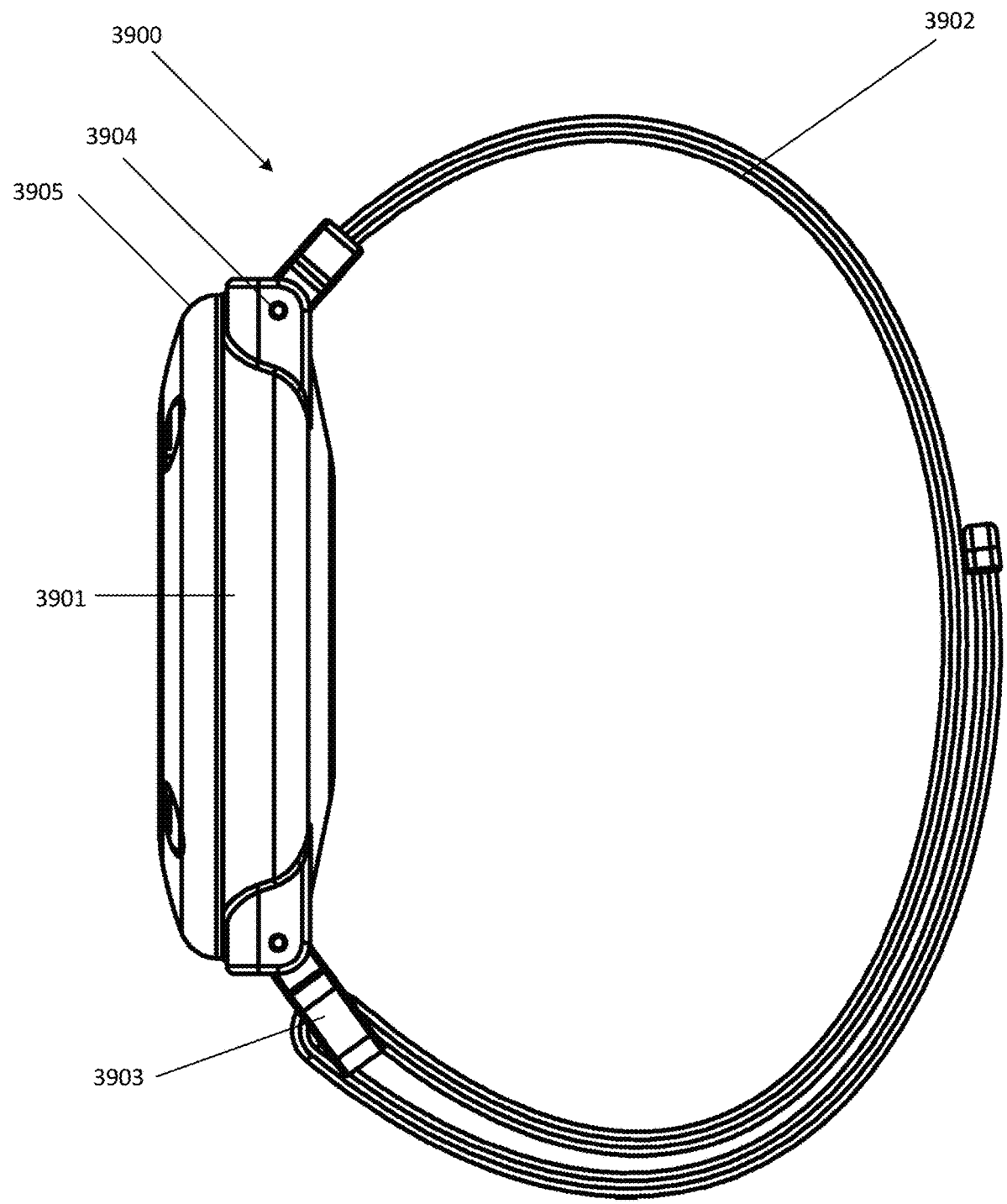
FIG. 39B shows a side view of a wearable device for monitoring a subject's performance of a physical activity, in accordance with an embodiment of the present invention.

FIG. 39B shows a side view of the device 3900. FIG. 39B shows the assembly 3905 on the left side and the strap 3902 on the right side. FIG. 39B shows that the strap 3902 may have slack that is adjustable through coupler 3903.

Figure 39C:
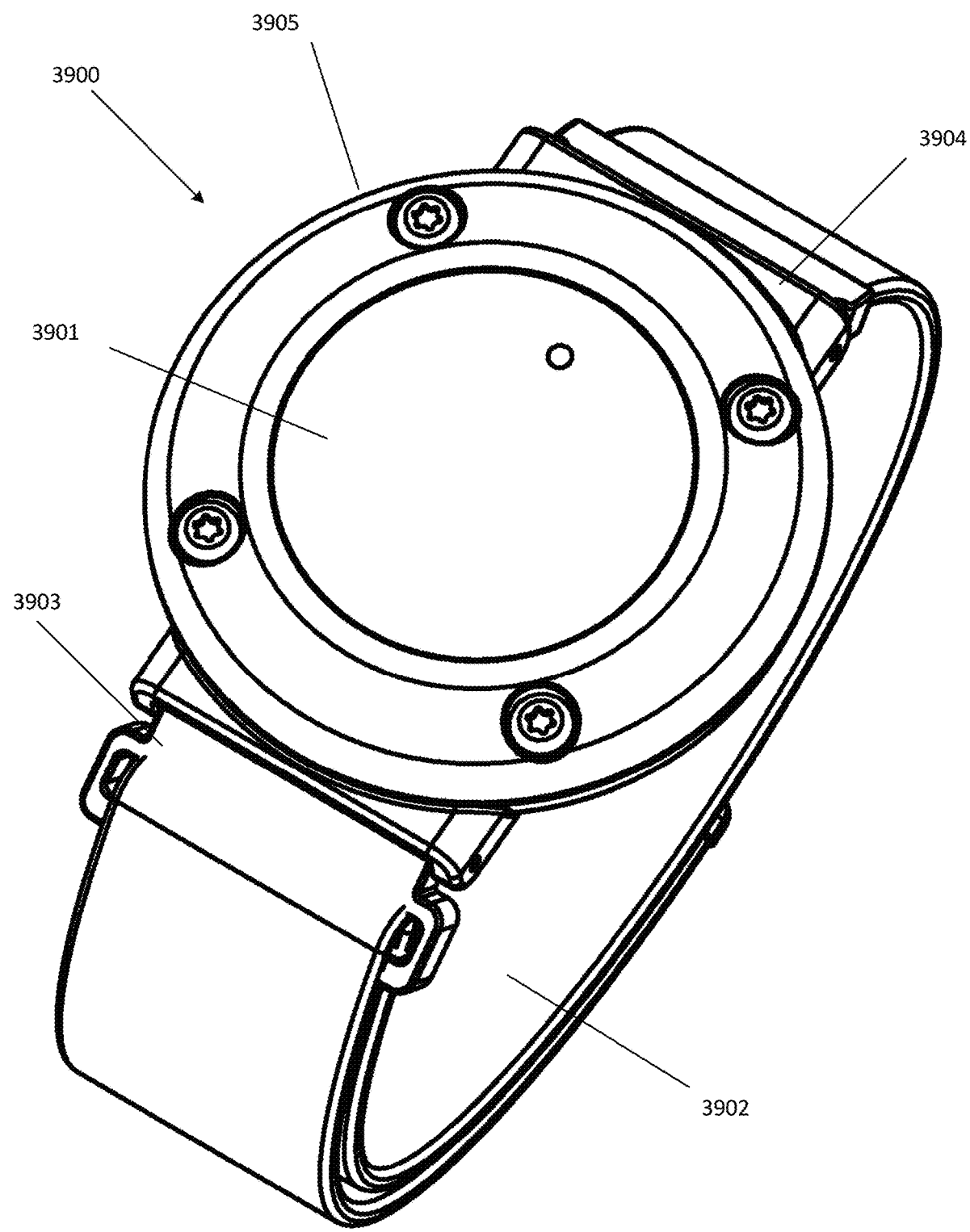
FIG. 39C shows an isometric view of a wearable device for monitoring a subject's performance of a physical activity, in accordance with an embodiment of the present invention.

FIG. 39C shows an isometric view of the device 3900. FIG. 39C shows the strap 3902 connected to both couplers 3903, 3904.

Figure 39D:
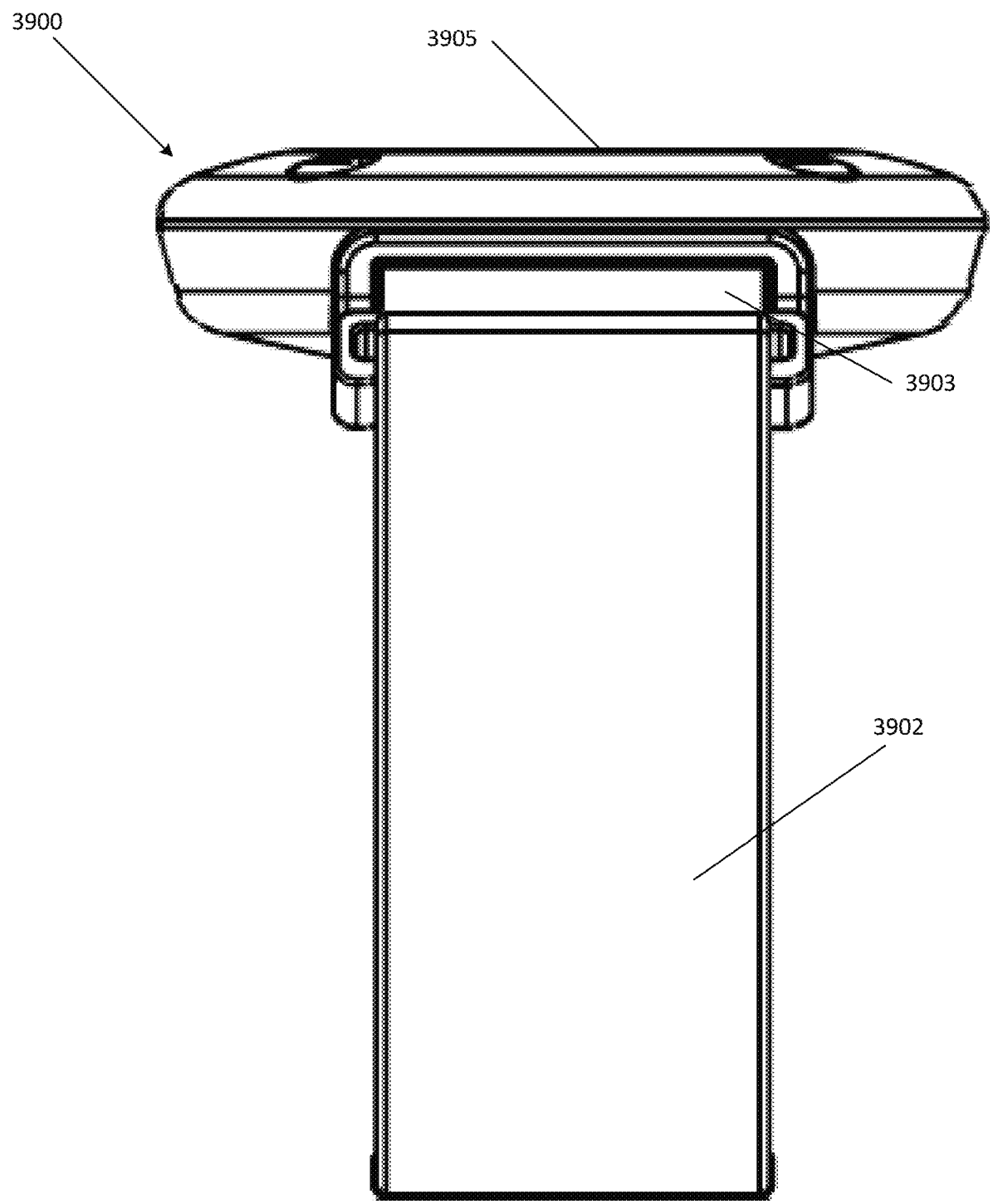
FIG. 39D shows a side view of a wearable device for monitoring a subject's performance of a physical activity, in accordance with an embodiment of the present invention.

FIG. 39D shows a side view of the device 3900. FIG. 39D shows the assembly 3905 on the top of the device 3900. The strap 3902 wraps around the assembly 3905 to the other side of the assembly 3905.

Figure 39E:
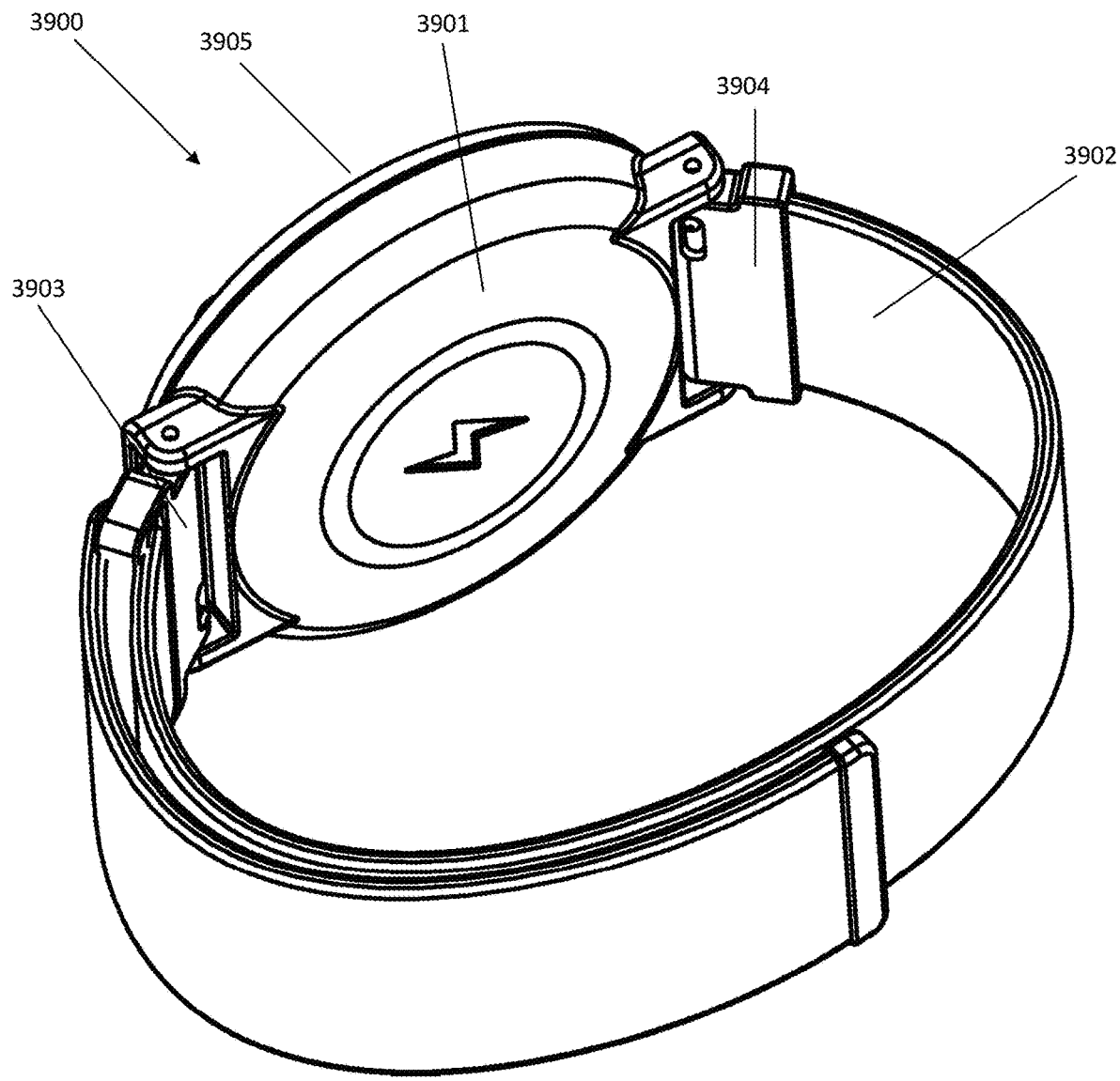
FIG. 39E shows an isometric view of a wearable device for monitoring a subject's performance of a physical activity, in accordance with an embodiment of the present invention.

FIG. 39E shows an isometric view of the device 3900. The back of the housing 3901 is shown allowing objects to be contained within the housing 3901.

Figure 5:
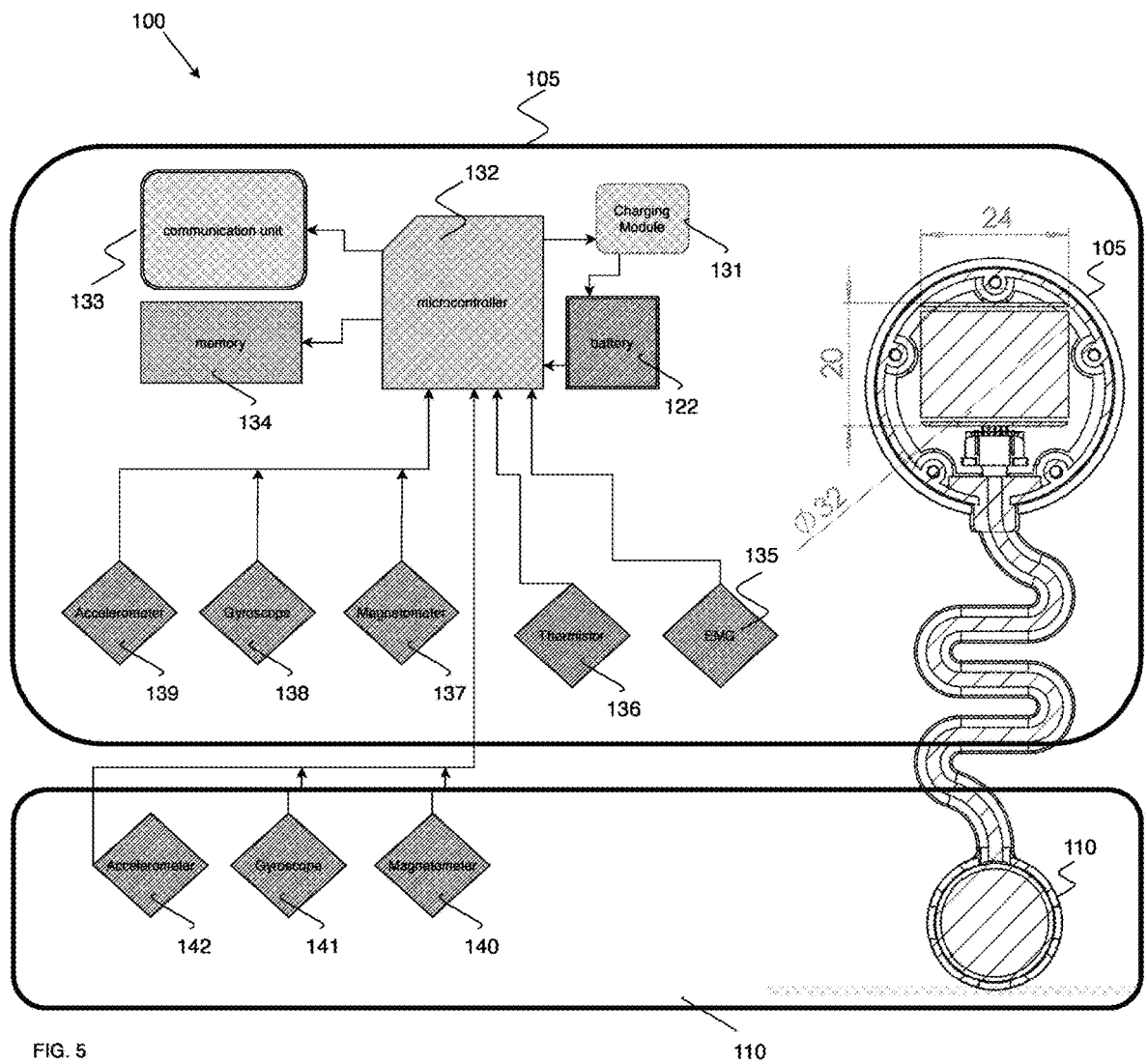
FIG. 5 is a diagrammatic view showing internal components of the device of FIG. 1 in relation to corresponding physical components of the device, in accordance with an embodiment of the present invention.

FIG. 5 is a diagrammatic view showing internal components of the device of FIG. 1 in relation to corresponding physical components of the device, in accordance with an embodiment of the present invention. In the embodiment of FIG. 5 the first assembly 105 has a set of sensors 105 that includes an accelerometer 139, a gyroscope 138, a magnetometer 137, a thermistor 136 (for measuring local temperature), and an electromyography (EMG) sensor 135 (for sensing muscle activity). The second assembly 110 has equivalent sensors which includes an accelerometer 142, a gyroscope 141, and a magnetometer 140. The sensors measure motions about a subject's joint, which are captured as motion data. The first assembly 105 also has a microcontroller 132 for managing the sensors and processing the motion data, and a memory 134 for storing the motion data locally. The first assembly 105 further includes a communication unit 133, such as a wired transceiver or a wireless transceiver (such as, but not limited to, WiFi, Bluetooth Low Energy (BLE), cellular, etc.), for transmitting the stored and/or processed sensor data to a destination. The first assembly 105 also includes a battery 122 configured to power the device 100 and a coupled charging module 131 configured to charge the battery 122.

Figure 6:
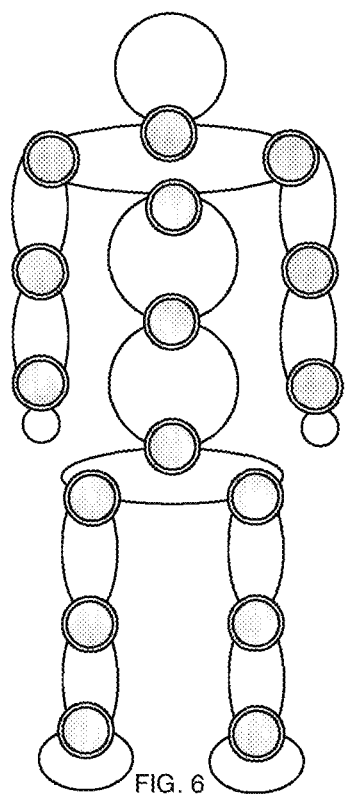
FIG. 6 shows locations on a subject's body having joints across which the device of FIG. 1 can be mounted for monitoring activity, in accordance with an embodiment of the present invention.

FIG. 6 shows locations on a subject's body having joints across which the device of FIG. 1 can be mounted for monitoring activity, in accordance with an embodiment of the present invention.

Figure 7:
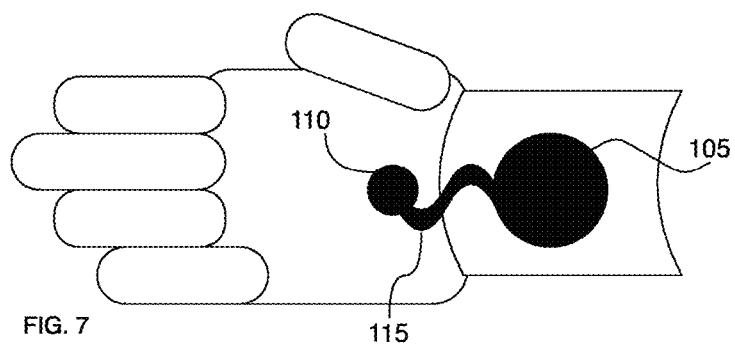
FIG. 7 shows an arrangement wherein the device of FIG. 1 is configured for mounting across the wrist joint of a subject, in accordance with an embodiment of the present invention.

FIG. 7 shows an arrangement wherein the device of FIG. 1 is configured for mounting across the wrist joint of a subject, in accordance with an embodiment of the present invention. In FIG. 7, the first assembly 105 of the device 100 is attached to the top of the subject's wrist and the second assembly 110 of the device is attached to the top of the subject's hand, such that the device 100 is positioned to record the motion around the subject's wrist joint 115. Using the recorded motion data, the device 100 can determine the differential angle, strain, etc. associated with such motion. The method of mounting the device to the subject can be, but is not limited to, adhering to the subject's skin using a biocompatible adhesive, or to an article of the subject's clothing, or other exterior garment worn by the subject.

Figure 8:
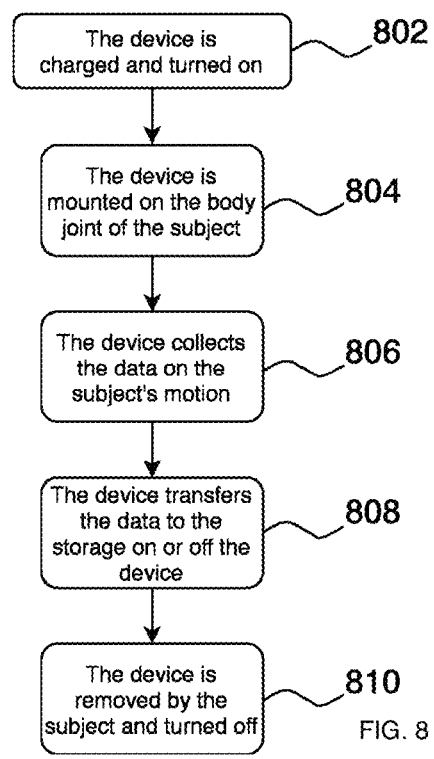
FIG. 8 is a diagram showing logical flow associated with using the device of FIG. 1, in accordance with an embodiment of the present invention.

FIG. 8 is a diagram showing logical flow associated with using the device of FIG. 1, in accordance with an embodiment of the present invention. In a first computer process 802, the device 100 is turned on. In some embodiments, the device 100 is turned on by the user, and in other embodiments, the device 100 is turned on by the detection of an event (e.g., motion or the subject entering a work area). In a second computer process 804, the device 100 is mounted across a body joint of the subject, such as across a wrist joint. In a third computer process 806, the device 100 collects the data on the relative motion about the body joint of the subject via the sensors configured in the device 100. In a fourth computer process 808, the device 100 transfers the data to storage located on or off the device 100. In some embodiments, the device 100 processes the data to determine metrics associated with the data, such as differential angle of the body joint, strain of the body joint, etc., and reports feedback to the subject or subject's employer based on the metrics. In a fifth process 810, the device 100 is removed by the subject.

Figure 9:
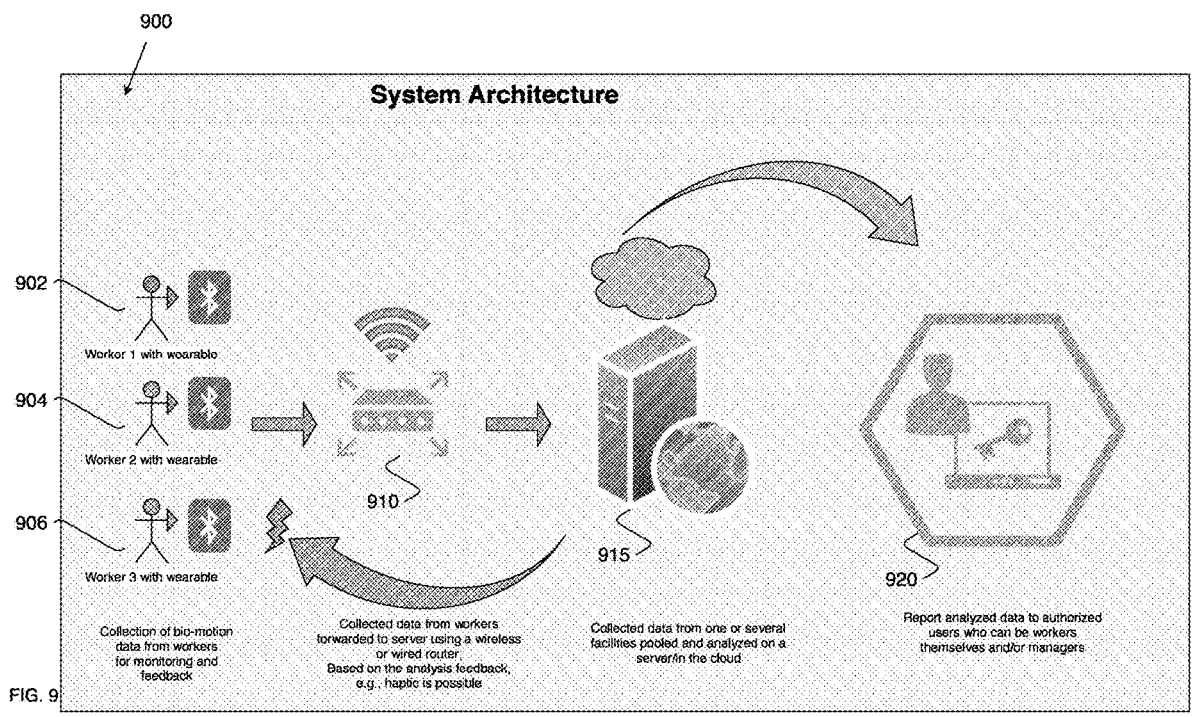
FIG. 9 is a diagram showing system architecture illustrating a context in which data from wearable devices, such as the wearable device of FIG. 1, are collected and processed in accordance with an embodiment of the present invention.

FIG. 9 is a diagram showing system architecture illustrating a context in which data from wearable devices, such as the wearable device of FIG. 1, are collected and processed in accordance with an embodiment of the present invention. The system 900 of FIG. 9 encompasses a four-part closed loop process. The system 900 includes devices 902, 904, 906 worn by corresponding subjects 1, 2, and 3 (e.g., workers) at one or several facilities. As a first part of the closed loop process, the devices 902, 904, 906 capture motion and physiological data of the subjects while they are performing physical activities. In embodiments, the devices are the wearable device of FIG. 1.

The devices 902, 904, 906 are communicatively coupled to a server 915 (e.g., cloud, local server, etc.) via a gateway 910 that includes wired and/or wireless routers. As a second part of the closed loop process, the gateway 910 gathers and forwards, by a wired or wireless method, the data captured by each of the devices 902, 904, 906 to the server 915. As a third part of the closed loop process, the server 915 aggregates (pools) the forwarded data and computes analytics based on the aggregated data. In the system 900, the server 915 is communicatively coupled to a computing device 920 of an authorized system user, who can be the subject and/or a manager of the subject. The server 915 reports the analyzed data for visualization on the computing device 920, which may be the subject's or manager's computer, tablet or mobile phone. The visualization summarizes the safety and performance of the subject's physical activities and the actionable items to improve the subject's personal safety and performance.

Figure 10:
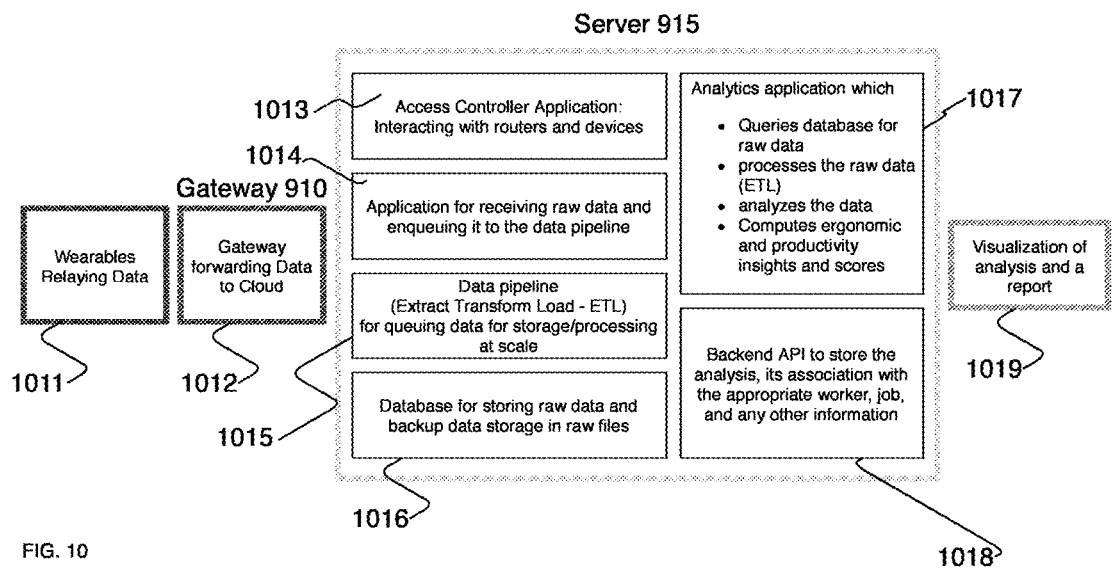
FIG. 10 is a block diagram illustrating processes carried out by the system architecture of FIG. 9, in accordance with an embodiment of the present invention.

FIG. 10 is a block diagram illustrating processes carried out by the system architecture of FIG. 9, in accordance with an embodiment of the present invention. As shown in FIG. 10, the wearable devices 902 include functional components 1011 for relaying data, and the gateway 910 includes functional components 1012 for forwarding the data to the server 915. As also shown in FIG. 10, the server 915 includes a controller application 1013 for interacting with the gateway (routers) and other devices, and an application 1014 for receiving raw data and queuing it to a data pipeline. The server 915 also include a data pipeline 1015 for queuing the raw data to store/process at scale, and a database 1016 for storing raw data and backup data in raw files. The server 915 further includes an analytics (data processing) application 1017 for querying the database for new raw data, processing the raw data via an Extract, Transform, and Load (ETL) methodology, and analyzing the processed data. The server 915 also includes a Backend API 1018 for storing the analysis in association with the appropriate subject, job, and any other information. As further shown in FIG. 10, the user device 920 includes components 1019 for providing a visualized report of the analyzed data.

Figure 11:
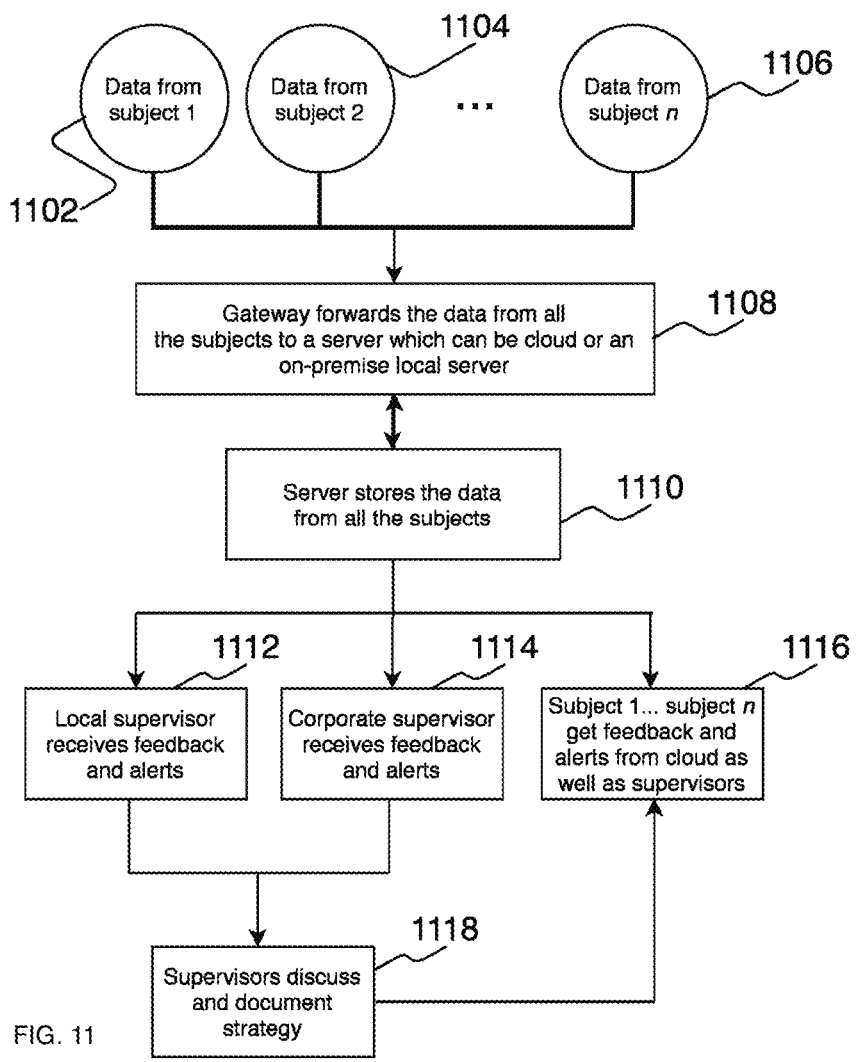
FIG. 11 is a diagram providing further details of information flow through the system architecture of FIG. 9, in accordance with an embodiment of the present invention.

FIG. 11 is a diagram providing further details of information flow through the system architecture of FIG. 9, in accordance with an embodiment of the present invention. As shown in FIG. 11, a first computer process 1102 captures motion data, via a device worn by subject 1, a second computer process 1104 captures motion data via a device worn by subject 2, and a third computer process 1106 captures motion data via a device worn by subject n. In embodiments, the devices are the wearable device of FIG. 1. A fourth computer process 1108, forwards, via a gateway, the data from all the subjects to a server (cloud and/or on-premise/local server). A fifth computer process 1110, via the server, stores the data captured from all the subjects. The stored data is processed by the server so as to generate feedback (e.g., visual reports and/or haptic in nature) and alerts from the data. A sixth computer process 1112 receives, via a local supervisor's user device communicatively coupled to the server, feedback and alerts generated from the data. A seventh computer process 1114 receives, via a corporate supervisor's user device communicatively coupled to the server, feedback and alerts generated from the data. An eighth computer process 1116 receives, via subject 1 . . . n's user devices communicatively coupled to the server, feedback and alerts generated from the data. A ninth computer process 1118 provides tools for the supervisors to discuss and document strategies.

Figure 12:
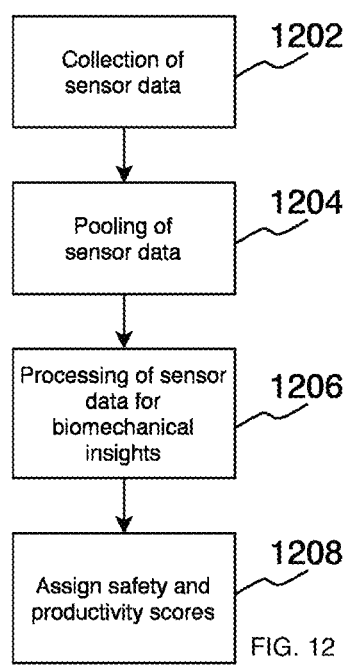
FIG. 12 is a further diagram showing data processing, in the system architecture of FIG. 9, of data to compute and assign a safety score, in accordance with an embodiment of the present invention.
Figure 13:
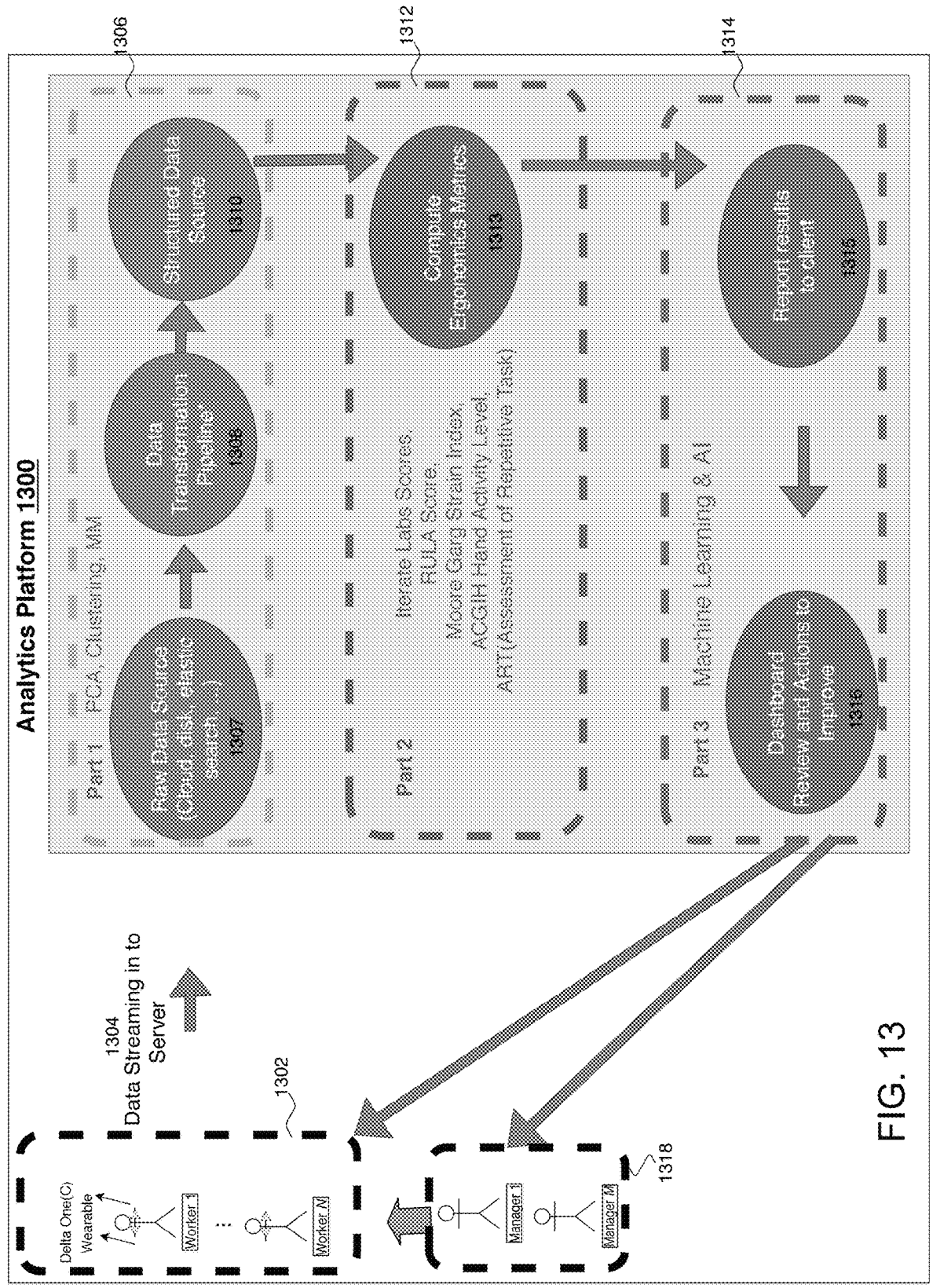
FIG. 13 is a diagram of the analytics platform starting by converting incoming raw data from the wearable as shown in FIG. 1 to structured output data, then computing ergonomic metrics, and finally reporting the data analysis to users and/or managers, in accordance with an embodiment of the present invention.

FIG. 12 is a further diagram showing data processing, in the system architecture of FIG. 9, of data to compute and assign a safety score, in accordance with an embodiment of the present invention. FIG. 12 only displays the summarized safety score but underlying its calculation are separate scores which are combined in a customizable way (i.e., different weighing mechanisms can be deployed) to form this actionable metric. In FIG. 12, a first computer process 1202 collects sensor data, such as by receiving the sensor data from wearable devices having sensors that capture the data in relation to the performance of physical activity/data by the subjects. In embodiments, the devices are the wearable devices of FIG. 1. A second computer process 1204 pools the sensor data for a given subject and across subjects. A third computer process 1206 processes the aggregated sensor data to determine biomechanical insights of the subjects from the data. This is where the analytics platform in FIG. 13 is used. This data processing includes, but is not limited to, data imputation, data filtering via an in-house extract, transform, and load (ETL) data pipeline detailed further in FIG. 18, and converting this data into a structured and standardized form as shown, e.g., in FIG. 15. A fourth computer process 1208 inputs the structured data and computes a set of safety and productivity scores related to various aspects of the subject's motions. Some scores address speed of motion (faster speeds introduce more energy in the joints), some scores address high-delta-angle (delta referring to the difference in angular values for sensors placed across a joint) motions, and others are cumulative in nature counting and reporting time spent above given threshold delta-angles. These individual safety scores are summarized via a custom mathematical weighing function to produce a final safety score. More details on how the scores are computed can be found in FIGS. 22, 23, and 26. The analytics platform, described in more detail in FIG. 13, supports adding any number of additional individual scores and including them in the final safety score as well. In this way, the analytics platform computes and assigns ergonomic safety scores to different parts of the motions associated with the physical activity of the user/subject. As an example of a productivity-based score, the volume of yaw, pitch, and roll can be computed as the volume of the convex hull of all yaw-pitch-roll points in three dimensions. This gives insights into the physical space occupied by the worker to complete the task. A larger volume-of-motions implies more time to complete the task. As another example, consider as a productivity-indicating score the ranking, via, e.g., percentiles, the time it takes to finish a given task (equivalently, the beforementioned convex-hull-volume can also be computed per cycle and expressed in a percentile form). This, in turn, requires the ability to extract single tasks from the data which is discussed further in FIG. 21 by leveraging machine-learning based algorithms.

FIG. 13 is a diagram of the analytics platform starting by converting incoming raw data from the wearable as shown in FIG. 1 to structured output data, then computing ergonomic metrics, and finally reporting the data analysis to users and/or managers, in accordance with an embodiment of the present invention. The diagram of FIG. 13 provides details of the analytics platform 1300 in the server 915 of the system architecture 900 of FIG. 9, in accordance with an embodiment of the present invention. The analytics platform 1300 receives 1304 raw data streamed to the server 915 from the wearable devices 1302 worn by subjects (e.g., but not limited to, factory workers). In embodiments, each wearable device 1302 is the wearable device 100 of FIG. 1. The raw data is stored in a data source (e.g., a database), which may be located in the cloud (e.g., via Amazon Web Services (AWS) or any other remote server(s), on local/on-premise disk(s) and/or server(s), etc. Note that it is not a requirement that the data be stored before entering the platform 1300, i.e., the platform supports streaming data directly from the wearable device or from any other location (other databases, servers, intermediate components, etc.).

The analytics platform 1300, in a first computer process 1306 called "Part 1" in the figure, retrieves 1307 the raw data from the data source, such as from the cloud via an AWS elastic search database but could be from any other data source such as on-premise storage devices or directly streamed. The analytics platform 1300, in the first computer process 1306, next queues 1308 the raw data in a data pipeline, where the raw data is cleaned which includes but is not limited to data imputation (e.g., statistical in-fill) and smoothing (e.g., with a Kalman filter). For the data imputation one can construct the joint distribution of the rows where all the data is present and then sample missing data columns from said distribution in relevant rows. Some Machine-Learning based techniques can easily be added and used for cleaning and pre-processing include clustering (unsupervised learning) for data grouping and outlier detection, principal component analysis (PCA) for data dimensionality reduction (the goal being to discover a representative subspace of the data simplifying further analyses among other benefits. The inputs to PCA would be the cutoff of total explained variance ideally at a kink in the total-explained-variance vs. number of principal components, etc.

Figure 18:
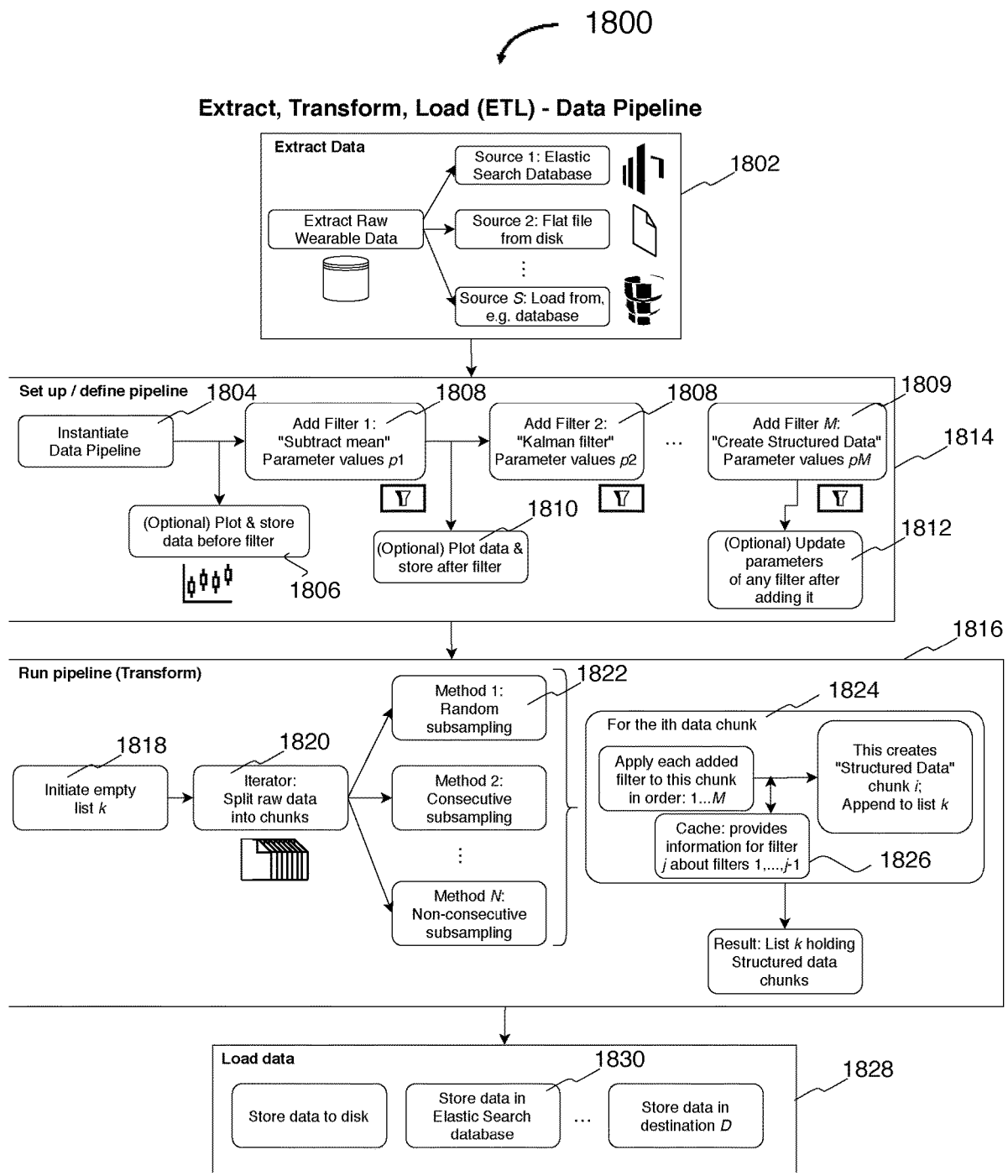
FIG. 18 is a diagram of the data transformation/filter pipeline converting incoming raw data to structured output data by leveraging, in turn, data filters.
Figure 19:
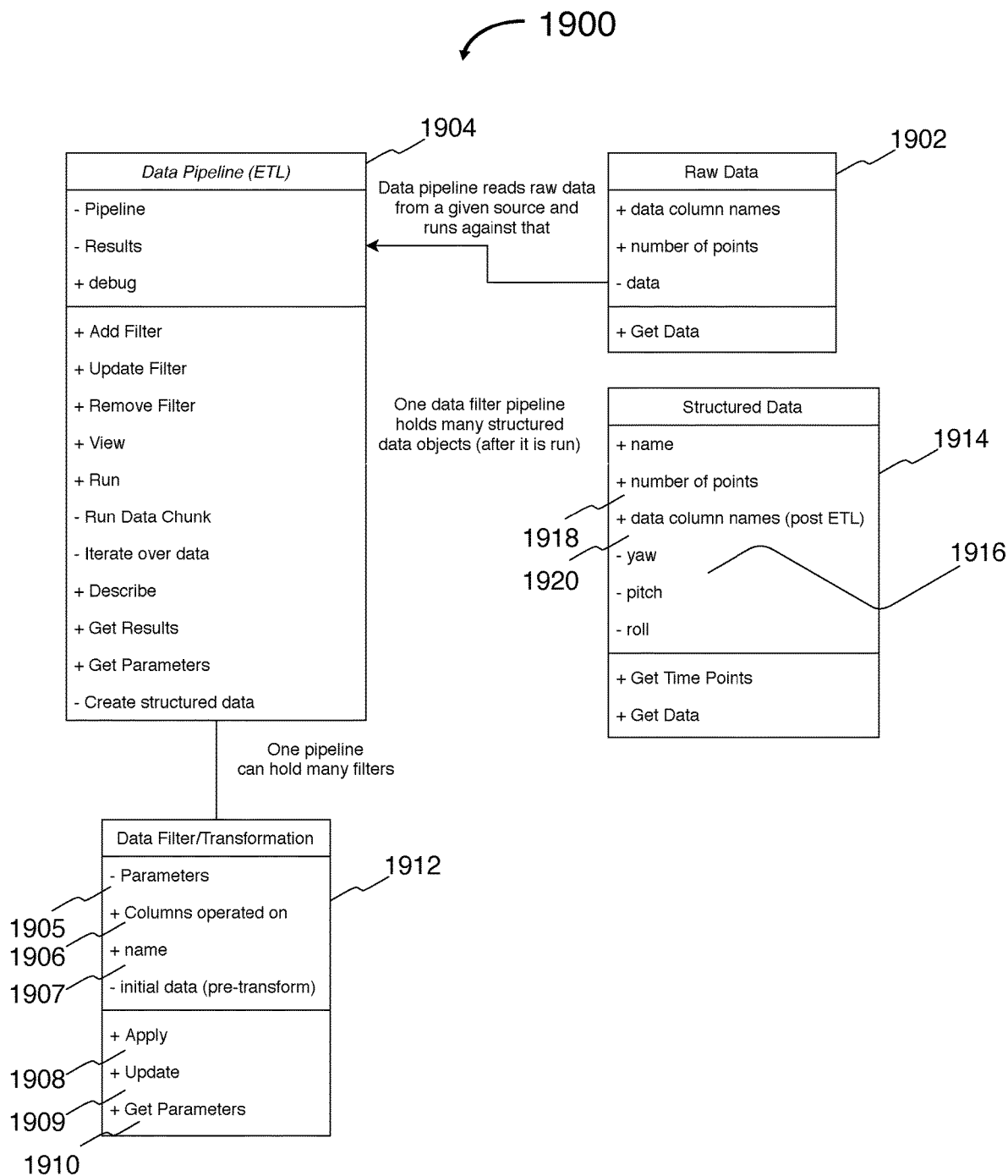
FIG. 19 is a UML Class diagram of the data filter pipeline of FIG. 18 and the various classes interacting with the pipeline from a coding implementation perspective, in accordance with an embodiment of the present invention.
Figure 20:
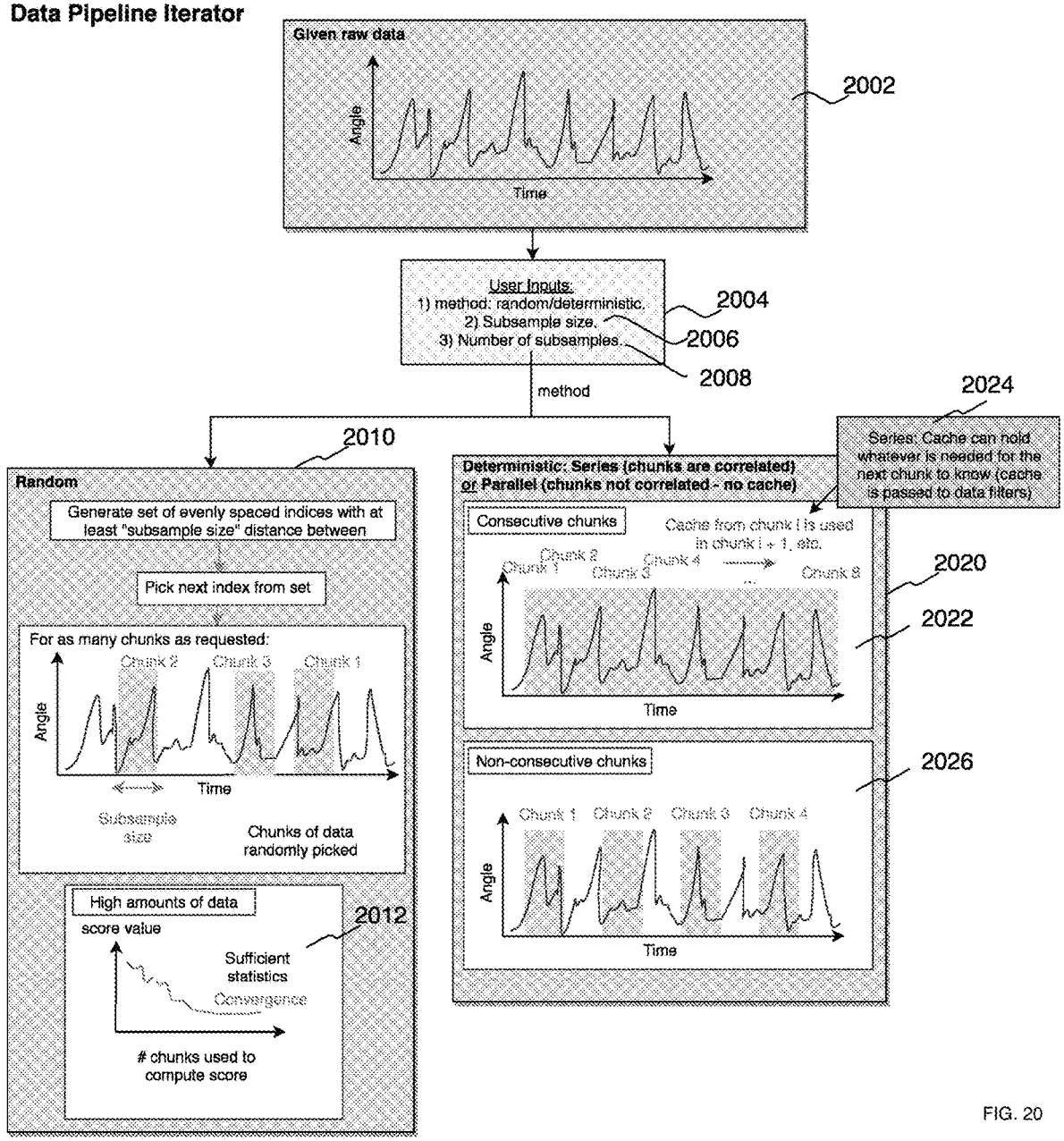
FIG. 20 is a diagram of the data filter pipeline iterator used by the data transformation filter in FIG. 18 which sub-samples the data in user-defined ways for higher quality and faster data-processing before score computations, in accordance with an embodiment of the present invention.
Figure 23:
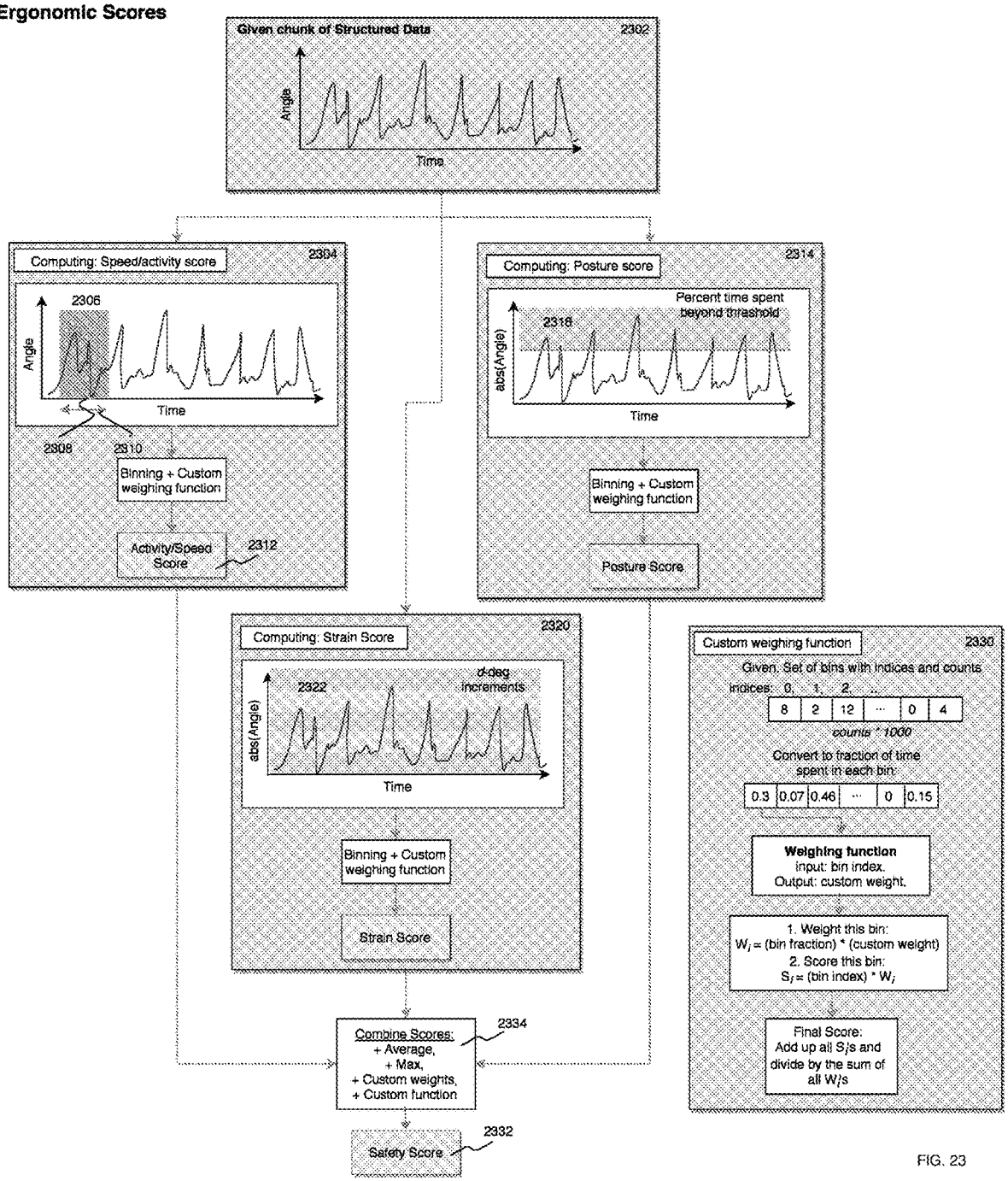
FIG. 23 illustrates in more detail than FIG. 22 the ergonomic scores computed to decide how ergonomic a motion is and the combination to provide the safety score, in accordance with an embodiment of the present invention.

The next step is entering the pre-processed data into an Extract, Transform, and Load (ETL) data pipeline to be covered in FIGS. 18-20. This pipeline can be viewed as an extension/generalization of the cleaning/pre-processing task. Here, the data goes through a series of filters discussed in FIG. 18 which simply takes in the data (and potentially only operates on a subset of the variables such as, e.g., acceleration), processes it as defined by the filter logic/algorithm, and outputs the data with the changes applied. Some examples of filters are: Centering the data, filtering out outliers/spikes (think of performing a Fourier transformation removing high-frequency components from the signal and transforming it back), addressing potential Gimbal lock issues, etc. The analytics platform 1300, in the first computer process 1306, then stores 1310 the transformed data in a structured data source. In embodiments, the structured data is data which adhere to certain interfaces/structures that programs and algorithms downstream can rely on. The structured data, covered in FIG. 15 with scores computed from this in FIG. 23, is configured to contain certain methods, contain certain variables, have a certain level of smoothness, etc., that the platform later relies on in computing safety scores and create customer insight reports. The structured data can be stored in whichever format is required, i.e., it can be stored in the cloud and/or on-premise or be streamed to the following process.

The analytics platform 1300, in a second computer process 1312 called "Part 2" in the figure, computes 1313 ergonomics metrics for a subject or group of subjects based on the cleaned and transformed data kept in the structured data source. The analytics platform 1300, in the second computer process 1312, then calculates a set of risk scores for each ergonomic metric, using assessment methods such as RULA scores, Moore Garg Strain Index, American Conference of Governmental Industrial Hygienists (ACGIH) Hand Activity Level, Assessment of Repetitive Task (ART), and Iterate-Labs-specific scores. On the final score, a set of individual scores/metrics are calculated pertaining to various parts of the repetitive motion which when combined via a mathematical custom weighing function (the simplest example being taking an unweighted average, but much more complex functions can be used) provides a summarized overall safety score. Details on how this is accomplished are given in FIGS. 22-23.

The analytics platform 1300, in a third computer process 1314 called "Part 3" in the figure, reports 1315 results based on the ergonomic metrics to the subjects and the subjects' managers. The analytics platform 1300, in the third computer process 1314, reports data which has been pre-processed, cleaned, filtered and used in the metrics computations leveraging machine-learning-based algorithms in the process to provide 1316, via a Dashboard, feedback to review 1302, 1318 and actions to improve the subjects' ergonomic performance, lower risk scores, and increase productivity so as to provide a safer working environment and increase company revenue.

Figure 14:
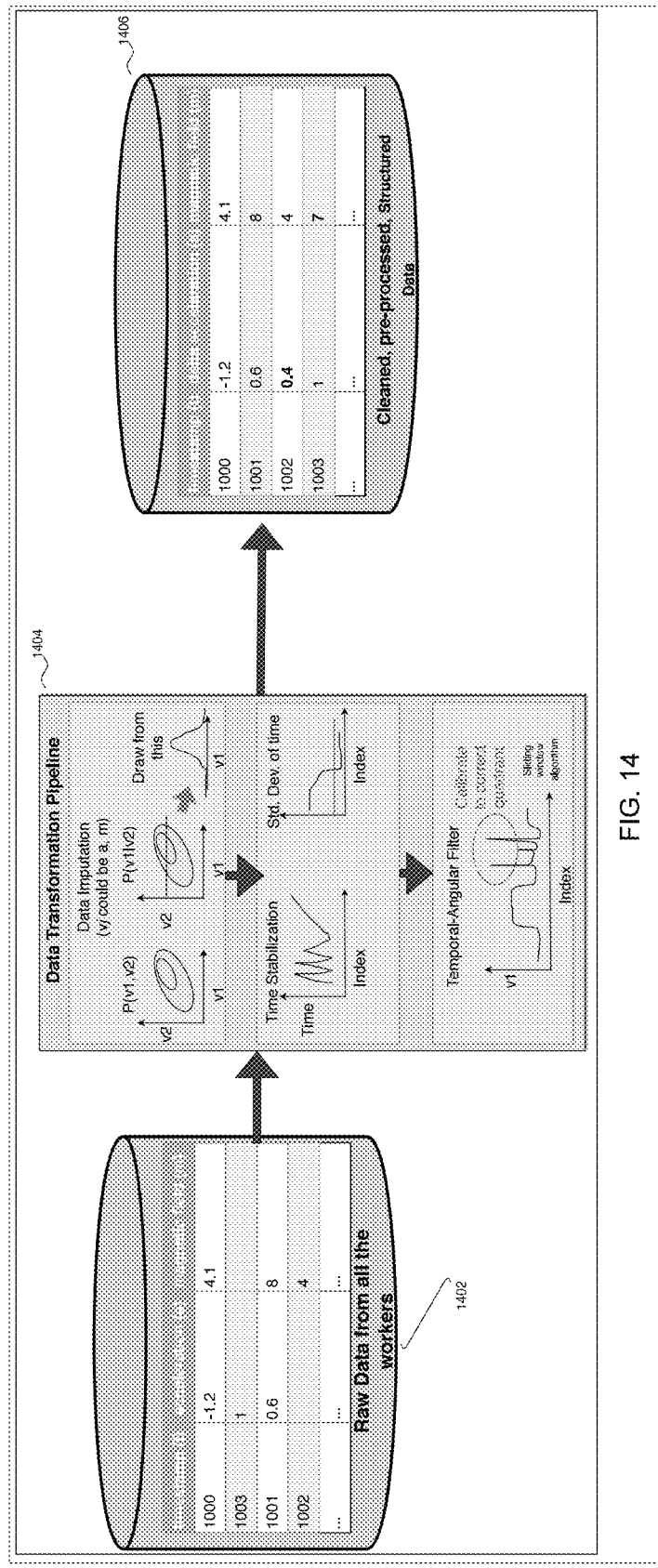
FIG. 14 is a diagram showing logical flow of data cleaning and structured data storage in the analytics platform of FIG. 13, in accordance with an embodiment of the present invention.

FIG. 14 is a diagram showing logical flow of data cleaning and structured data storage in the analytics platform of FIG. 13, in accordance with an embodiment of the present invention. The source of the raw data 1402 can be in any form, it is up to the developer to create interfaces to various sources. For example, the data can come from a csv file on disk having been collected by the wearable sensors. Another "raw-data class", as said data classes can be referred to, can be created to handle sensor data streaming directly from the device. In this case then, the data is not first stored to disk in a csv file but is directly streamed to the analytics platform in FIG. 13. The ETL tool that is the data transformation pipeline 1404 detailed in FIG. 18 is the way it integrates with the data subsampling method, an embodiment of which is discussed in detail as part of FIG. 20. In embodiments, this is done with a "Raw Data" class, as shown in the UML diagram of FIG. 19. The data filters together perform the "transformation" part of the pipeline to produce structured data 1406.

The method starts with raw, unfiltered, and unprocessed, motion data 1402 streamed from the wearable devices of all subjects (workers) and, e.g., stored in a database (the method of pre-processing and cleaning is indifferent to how the raw data is stored). The method next loads/queues data in a data transformation pipeline 1404, where it is cleaned and filtered by going through an extract, transform, and load (ETL) process/data pipeline within the server (cloud or on-premise supported) using various computational methods, including data smoothing with a Kalma filter, data imputation via statistical representation and filtering (shown in the top subplot in 1404), time stabilization if needed by looking at the standard deviation of time (shown in the middle subplot of 1404), and temporal-angular filtering techniques to handle Gimbal locks (illustrated in the bottom subplot of 1404), among other methods, and any additional custom filters can be added to the pipeline. The method then stores 1406 the cleaned, pre-processed, data structured in a database also supporting cloud or on-premise solutions. The point of this step is to accept raw and unfiltered data on one end of the application and turning it into structured data which can be analyzed and mined for actionable insights as it relates to improving workforce productivity and decreasing the risk of injuries.

FIG. 15 is a table illustrating structured worker motion data 1406, in accordance with an embodiment of the present invention. Such motion data may be structured data 1310 produced by the first process 1306 of FIG. 13. Note that this is just an example data format. The invention supports multiple different data formats where the table would have different columns/information from sensors and this can be controlled at the user level. For example, in one firmware version of the wearable only the delta values of yaw, pitch, and roll are transmitted. In another data format, acceleration and velocity is included as well, and so on. In embodiments, the data is represented as a class in an object-oriented paradigm with methods and attributes, with more detail of those in FIG. 19, improving the speed, readability, modifiability, and usability of the program further downstream.

Figure 16:
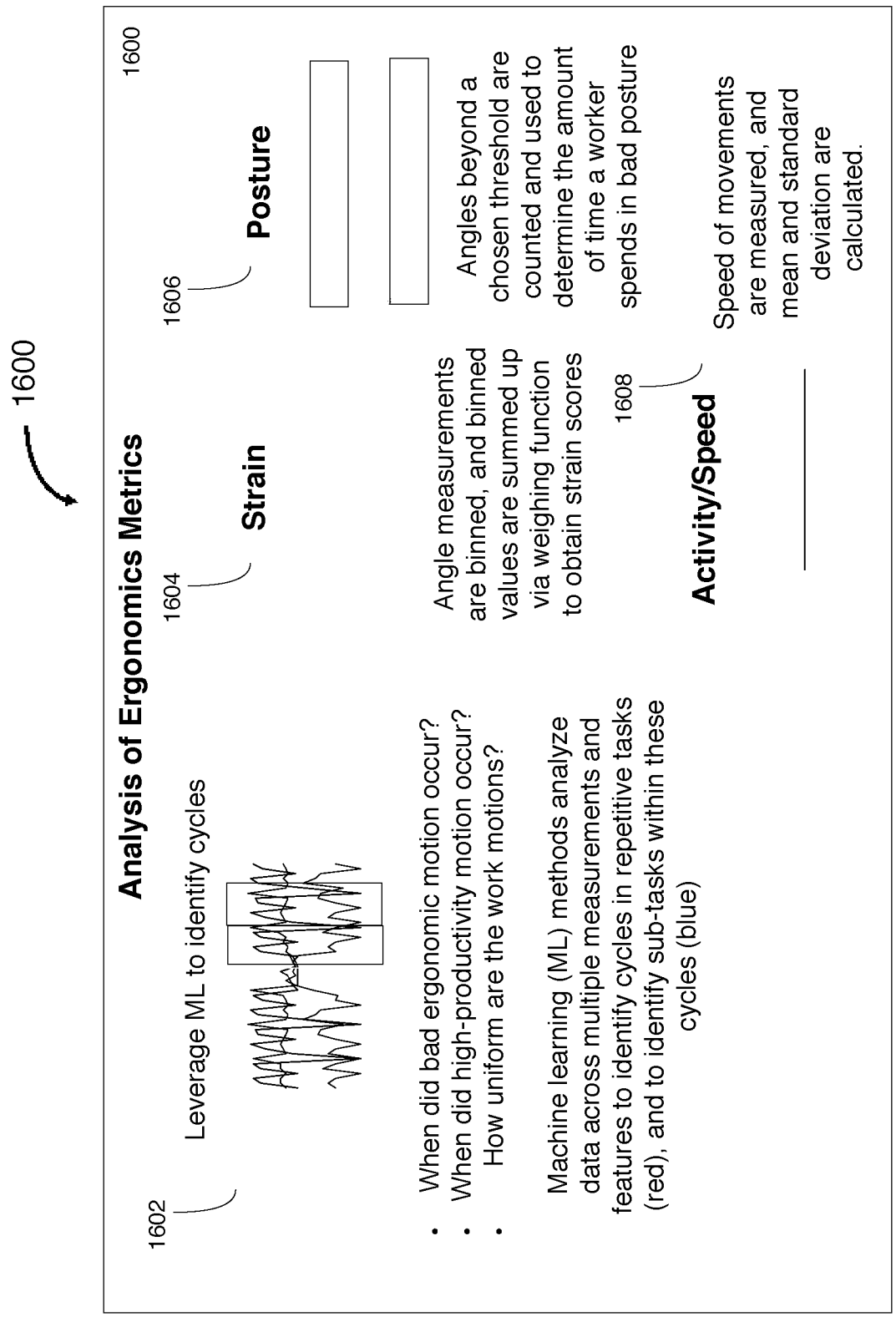
FIG. 16 illustrates concepts pertinent to analysis of data associated with ergonomic activity, in accordance with an embodiment of the present invention.

FIG. 16 illustrates concepts pertinent to analysis of data associated with ergonomic activity, in accordance with an embodiment of the present invention. In FIG. 16, the cleaned, filtered, and processed data of FIG. 15 is analyzed 1600 to calculate various ergonomics metrics for an individual subject or group of subjects covered in more detail in FIG. 23. The analysis leverages machine-learning-based tools 1602, discussed in more detail in FIG. 21, which extract the cycles from the tasks performed focuses on the intensity, duty-cycle, and frequency of the user's captured motions by the wearable device but can readily extend to include additional features of the data (such as in-depth cycle analysis). The ergonomics metrics include strain 1604 posture 1606 and activity 1608 that is calculated by binning angle motion measurements and applying a custom weighted sum function on the binned values to obtain strain, posture, and activity scores. The custom weighing function, shown in FIG. 23, takes in the set of bins and the set of associated counts in said bins. As an example, consider a "constant" weighing function as implemented in the present product. Say we have M bins. This function applies the weight 1/M to each count value and add to a running sum. After all bins are processed the final value is the average bin. In this case, assume M=10 and that there is 1 count in each bin. The value computed using the "constant" method is 5. This bin value can then be converted to a scale from 0-7. By tuning the number of bins one can get more or less severe scores for the same data. In some other embodiments, a "linear" weighing function can be used, which takes the counts in the first bin and multiplies by 1, then the counts in the second bin and multiplies by 2, and so on adding up the score and normalizing. In some other embodiments, a quadratic weighing function can be used, which would place more weight on counts in larger bins. These weighing functions have parameters which can also be tuned/learned to data collected to provide accurate scores.

Another approach used in some embodiments is a "distribution method" which computes statistical properties of the distribution-of-angles and their summary is used as a measure of bad strain. Specifically, the mean, variance, skewness, and higher moments are computed. A larger mean implies a less ergonomic motion, the same for larger variance. The skewness can inform about a tendency to perform the task at positive angles compared to negative or vice versa which can be unergonomic if a preference towards one sign of angles occur. In terms of deciding specific thresholds for the moments in terms of when they turn unergonomic, data needs to be collected to fit/learn these thresholds. Any other custom, user-defined, function for summarizing this score can be used as well in some embodiments. The metrics may also include cumulative values where time spent beyond certain thresholds are leveraged. As part of the analysis, the method leverages machine learning techniques to identify cycles in the measurements of a subject or group of subjects. In particular, the machine learning techniques analyze the data across multiple measurements and features to identify cycles in repetitive tasks (red box delineation in the top left plot to the right side) and to identify sub-tasks within these cycles (blue delineation in the top left plot to the right side). More details on this method is discussed in FIG. 18 next. Special data filters can be devised and added to the data pipeline that can help identify when non-work periods are encountered (breaks, bathroom visits, etc.).

Figure 17:
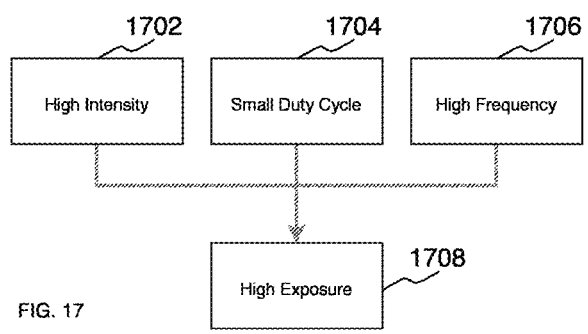
FIG. 17 is chart illustrating logical flow associated with ergonomics scoring carried out by the analytics platform of FIG. 13, in accordance with an embodiment of the present invention.
Figure 24:
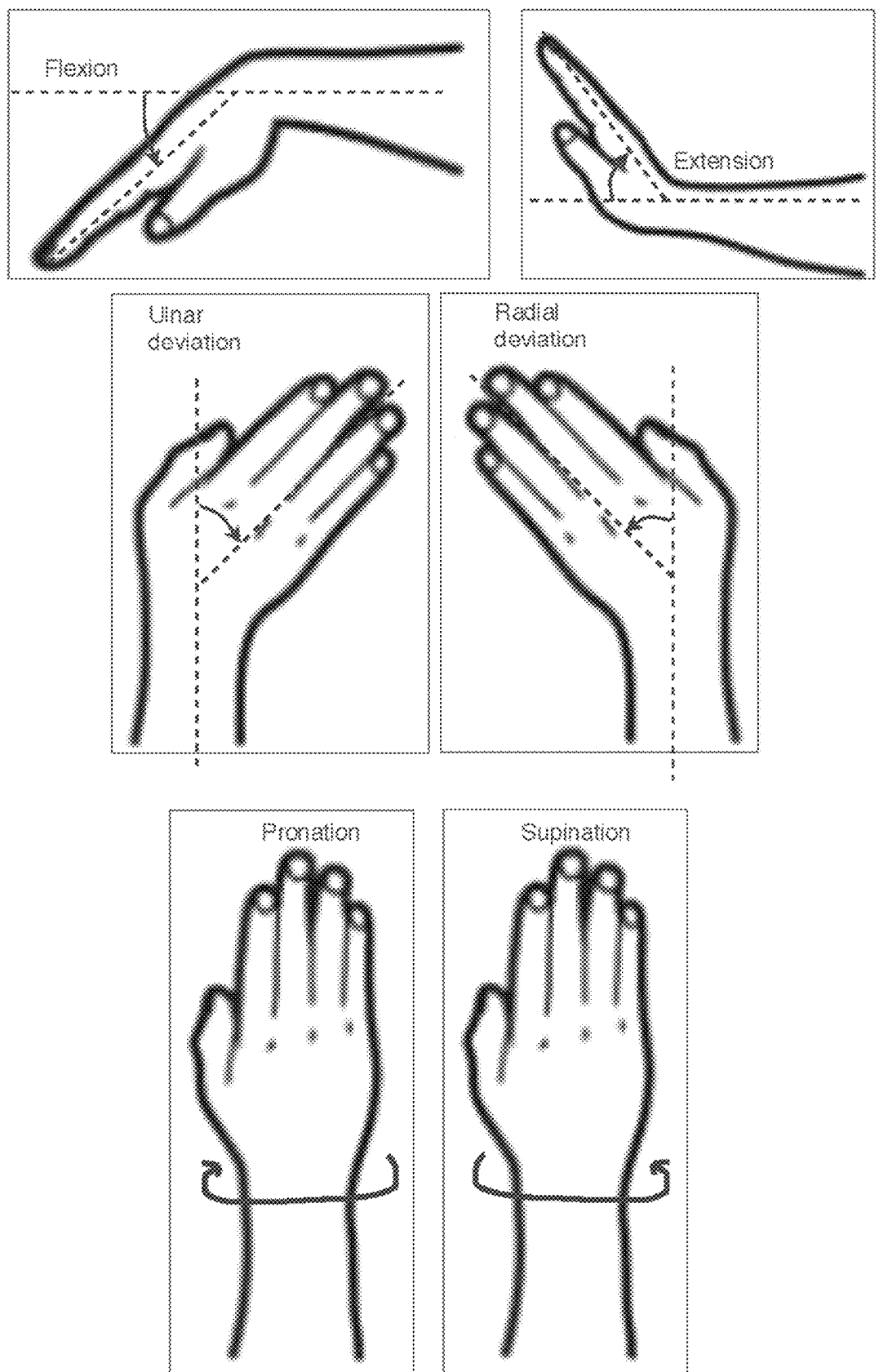
FIG. 24 illustrates types of wrist motions used in the ergonomic scoring, in accordance with an embodiment of the present invention.

FIG. 17 is chart illustrating logical flow associated with ergonomics scoring carried out by the analytics platform of FIG. 13, in accordance with an embodiment of the present invention. These pertinent concepts can be applied to perform ergonomic evaluation of the radial/ulnar angle, flexion/extension angle, and pronation/supination angle parameters of the subject's wrist motions, such as shown in FIG. 24. These pertinent concepts include high intensity 1702, small duty cycle 1704, and high frequency 1706 and are applied to such parameters of the subject's joint motions to calculate a safety score, which represents the high exposure 1708 of the motion. In the embodiment of FIG. 17, the safety score is calculated with inspiration from the RULA assessment method shown and discussed in FIG. 27.

FIG. 18 is a diagram of the data transformation/filter pipeline converting incoming raw data to structured output data by leveraging, in turn, data filters. The pipeline in totality 1800 converts incoming raw data 1802 to structured data 1828. As examples, some embodiments support loading from and Elastic Search (ES) database (Source 1 in the FIG. 1802), a flat file from disk (Source 2) or other database sources (represented as a generic Source 5) such as Microsoft SQL Server, PostgreSQL, MySQL, MongoDB, cloud-native systems such as, e.g., Amazon Web Services' simple storage service (S3) technology and/or Athena, etc. The data can originate from any source as long as appropriate code can be written to bring the data in the format of, e.g., a Python pandas DataFrame or a Python numpy array which can both be read by the raw data object class of the platform. It is up to the developer to write such glue scripts. In the present embodiments ES and flat files are supported as raw data sources. The data (transformation) pipeline 1814 starts by initializing the pipeline 1804 and adding data filters 1808 to it. The filters 1808 are registered in an internal database of the data pipeline object. Each filter has its own set of parameters which can be modified either before or after adding it to the pipeline (e.g., a smoothing filter may have a window size) 1812. The filters 1808 can include a transformation of its incoming data which simply subtracts the mean from said data (Filter 1). Another filter can help smooth the data and turn it into a continuous time series—such as a Kalman filter—with benefits to subsequent data manipulations (Filter 2). Note that the last filter in the pipeline is required to construct the structured data object 1809 discussed in FIG. 19. In some embodiments this can be done automatically without the user needing to do this and a check can be made to see if the last filter indeed was of this structured-data-construction type and apply as needed. For debugging purposes, and increased insights, in embodiments, the pipeline supports a debugging feature where it can plot the data coming into any of its filters before 1806 and after 1810 entering a filter. Next, the data filter is run 1816 with the raw data as input. To this end, a list is first initiated 1818 which will hold the data chunks output from the filter. Then, a data filter pipeline iterator 1820, as discussed in FIG. 20, processes the data, potentially in parallel, as can be the case for random sampling 1822, and generally is dependent on how the application is run, by splitting it into chunks 1824 (simply defined as subsets of data). In some cases, one data chunk may depend on some parameters and information from a filter having processed a previous data chunk. In this case, a cache can be handed off between the data chunks storing any information needed 1826, which in turn can be populated by the filters. This, therefore, is a way to introduce a dependency between data chunks which can be necessary in some embodiments. For example a filter can leverage knowledge of the past level of yaw angles to perform a given action in this chunk (e.g., a level-change filter or similar). For each data chunk, regardless of what the iteration method is, the filters are now applied in sequence of registration (as mentioned earlier) with their given parameters. This is the "transformation" part. Finally, the transformed data is "loaded"/stored to either a disk, in a database, or some other destination 1828. This is up to the use-case to mandate. In the some embodiments, in production an elastic search database is used 1830.

In general, a data filter is a function that takes in data, performs a mathematical operation/transformation of the data (which can be as simple as filtering the rows or the columns), and returns the transformed data to the calling function including a description of what occurred such as whether a column was added—how a column was transformed—which rows were altered—etc. for potential debugging and to collect helpful meta-data. An example of a data filter/transformation can be to add or subtract a fixed amount of degrees from the incoming angular values (e.g., if it is known that the sensor is off by a constant amount of degrees). As another example, it can be a mean-shifting filter: Subtract the mean from the data and return mean-zero data. As yet another example, a filter can combine two columns into a net new column and remove the previous two columns. Many other transformations are possible such as smoothing, Kalman filtering, and other such data de-noising techniques.

FIG. 19 is a Unified Modeling Language (UML) Class diagram of the data filter pipeline of FIG. 18 and the various classes interacting with the pipeline from a coding implementation perspective, in accordance with an embodiment of the present invention. FIG. 19 provides an illustration of an example implementation in an object oriented way. For more details on an embodiment of the data filter pipeline see FIG. 18 as well. The Data Pipeline (an extract, transform, load (ETL) pipeline) 1904 can hold many data filters 1912, each filter performing a transformation of the raw data 1902. It has a set of parameters 1905 and a user-defined name 1907 for easy reference. It also contains a list of column names in the data on which it operates 1906. Each filter has an "apply" method 1908 which, in turn, is called by the data pipeline 1904. The filter can also have its parameters updated 1909 and returned 1910 to the user as well. When each filter is instantiated, its parameters are initialized with parameters defined by the developer having implemented the filter. As discussed in FIG. 18, the final filter in the pipeline needs to be a filter which creates a structured data object 1809.

With respect to FIG. 19, the purpose of the structured data object 1914 in embodiments of the present invention is discussed. The structured data object 1914 works as an interface for further downstream processing such as when computing the scores. In this sense, it serves as a promise that the data has been filtered and that specific part of the data is available 1916 (such as the yaw, the pitch, and the roll). The structured data class 1914 also offers information regarding the data such as how many points there are 1918 and the column names remaining after filtering (if, e.g., a filter removes a column) 1920. More generally, it can hold other key information as needed post-ETL and can thus readily be extended as the platform grows without requiring API changes further downstream (Parts 2 and 3 in FIG. 13).

FIG. 20 is a diagram of the data filter pipeline iterator used by the data transformation filter in FIG. 18 which sub-samples the data in user-defined ways for higher quality and faster data-processing before score computations, in accordance with an embodiment of the present invention. The subsampling may be for multiple use-cases such as higher filter quality (by applying the filter to smaller chunks of data at-a-time) and faster data-processing before score computations (only processing enough data to be statistically conclusive—but not technically processing all data). Building on this—the iterator in embodiments can serve two purposes. First, it helps speed up the data processing since it can process the data in separate chunks. Second, for cases where the amount of data is huge, the iterator can draw random chunks 2022 from the data and the score is monitored until convergence sets in. In that case, we rely on a form of sufficient statistic. Given raw data 2002, the user can select a set of methods with which to process said data 2004 such as randomly drawing chunks 2010 and computing scores from that or to process the data deterministically 2020. Also as an option to how large each chunk/subsample should be during the processing 2006; the user selects this.

For example, if we have 8 hours of work collected each chunk can constitute 5 min. The user also selects the number of subsamples/chunks to collect 2008. Starting with the deterministic approach 2020 in FIG. 20, in turn, embodiments provide two options. First, the user can choose to process the data consecutively 2022. Parameters can be passed from one data chunk to the next if needed 2024 (if the chunks are correlated, i.e., the results from processing chunk i is relevant to processing i+1). In this case, the data cannot be processed in parallel and a cache is used to pass information between the chunks. But if the chunks are not correlated in this way, the iterator supports parallel processing of the data. In the second case, we can process the data non-consecutively 2026. This means having a gap between chunks but they are evenly spaced apart.

In the case of random processing 2010 we draw chunks at random (without replacement) and use those to compute the score. It is optional whether to use a convergence metric 2012 (such as the score) to decide if enough chunks have been processed to get an accurate value for the score. In this case, a data filter could be added to detect breaks, but if the data amount is high enough this may not be needed. In any case, this demonstrates another good use of data filters 1808 as shown in the embodiment of FIG. 18. In summary, the data iterator of FIG. 20 is helpful to break down the data intelligently and process what is needed to establish a strong value for the scores.

Figure 21:
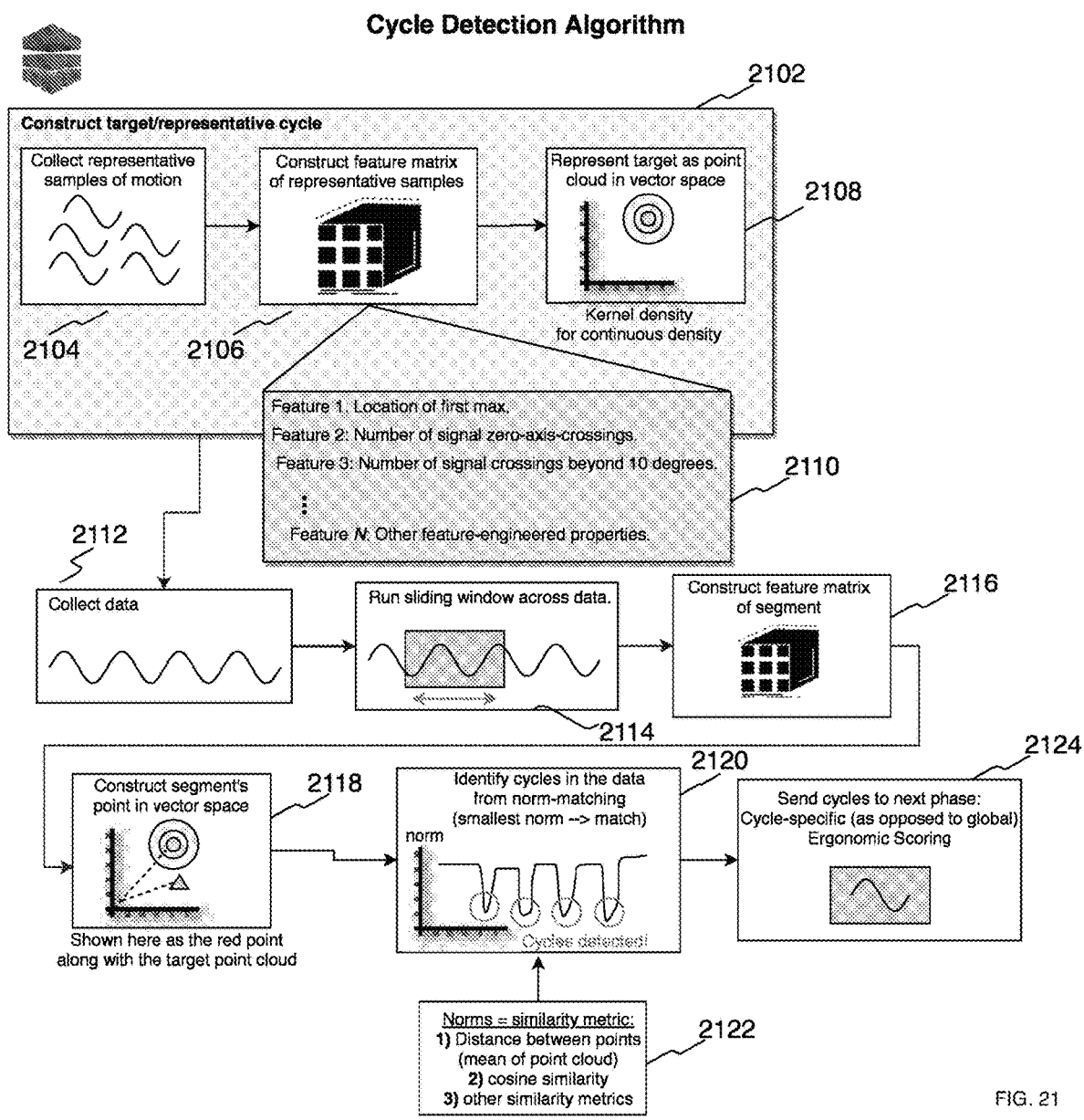
FIG. 21 illustrates the machine-learning based process for detecting cycles in the wearable-collected data, in accordance with an embodiment of the present invention.

FIG. 21 illustrates the machine-learning based process for detecting cycles in the wearable-collected data, in accordance with an embodiment of the present invention. This method of FIG. 21 starts by collecting a set of representative samples 2102 of the task being performed. Collecting 10-20 samples is typically enough 2104. A sample in this context is defined as follows: It consists of data collected from the sensors in the same way the data would be collected when the invention is deployed in production. The difference with the full-deployment, or productionized, case is that a sample, in this context, is the data collected for performing the task at hand a single time. The task with respect to the method of FIG. 21 means a full cycle of performing the duties at a work station—for example, this can involve taking an empty box, filling the box with items hand-picked off of a conveyor belt, taping up the box, moving the box to a pallet for shipping, that is all together a full cycle—a task. The worker then repeats this task—what was named a sample above—over and over again during the full 8-hour workday. A sample then consists of a set of time series data from the wearable sensors which is limited to a single task. There can be slight variations in the way each task is performed which explains the collection of multiple repeated tasks. Then, a feature matrix is constructed for each sample 2106. The features are engineered to maximize detecting the cycles in the data. This is up to the engineer to design but some features can be the location of the first maximum in the data, the number of signal zero-axis-crossing, the number of crossing beyond a certain finite angle, and so on until N features are collected 2110. In the present implementation ~100 features are collected. In embodiments, one can perform Principal Component Analysis (PCA) on these features as well to reduce the space from N (assumed >>1) to a lower number depending on the explained variance and method used to decide the cut-off of number of components. Having converted the sample into a matrix allows us to think of the samples as a point in an N-dimensional space 2108. Since we collected multiple samples technically the point in space is more like a cloud of points in space. In embodiments, one can use kernel density estimation to smooth out said point cloud to a continuous function. Next, we are given a sample of newly collected data 2112 and need to decide where in the data the tasks occur. To do this, a sliding window is moved across the data 2114. For each window, a feature matrix 2116 is constructed in the exact same way as when constructing it for the initial representative samples. The sample is now a single point (or equivalently, a delta function if using a continuous function perspective)—shown as a triangle—along with the point cloud just constructed 2118 represented as concentric circles. The engineer now needs to decide on a distance metric between this new point and the existing point cloud 2122. Some ideas are cosine similarity (where a mean of the point cloud is used) or a Kullback-Leibler (KL) divergence but a person skilled in the art can create the best fitting norm. We use the KL in the embodiment of FIG. 21. Whatever metric, it is computed and plotted 2120. As the window slides over the data (the user decides the window size and how much it slides by), the norm becomes small in some regions and larger in other regions 2120. Since the norm represents a distance, we find a cycle when it takes the smallest values. We can leverage additional information about when the cycles occur in that we know they are periodic in nature which can help smooth out the results more and give more accurate conclusions. Specifically, when a cycle has been identified in a given region we don't look further there. Having collected the cycles, various scoring statistics can be gathered 2124 such as how long time the specific cycle took, what the angular range explored was—the more extreme the less productive, etc. This all becomes part of the report back to the worker and/or manager, such as in part 3 of FIG. 13. For simple cyclical data, in embodiments, one can also use Dynamic Time Warping (DTW) instead of constructing the feature matrix, but we find that for very complex data, the machine-learning based approach outperforms DTW.

Figure 22:
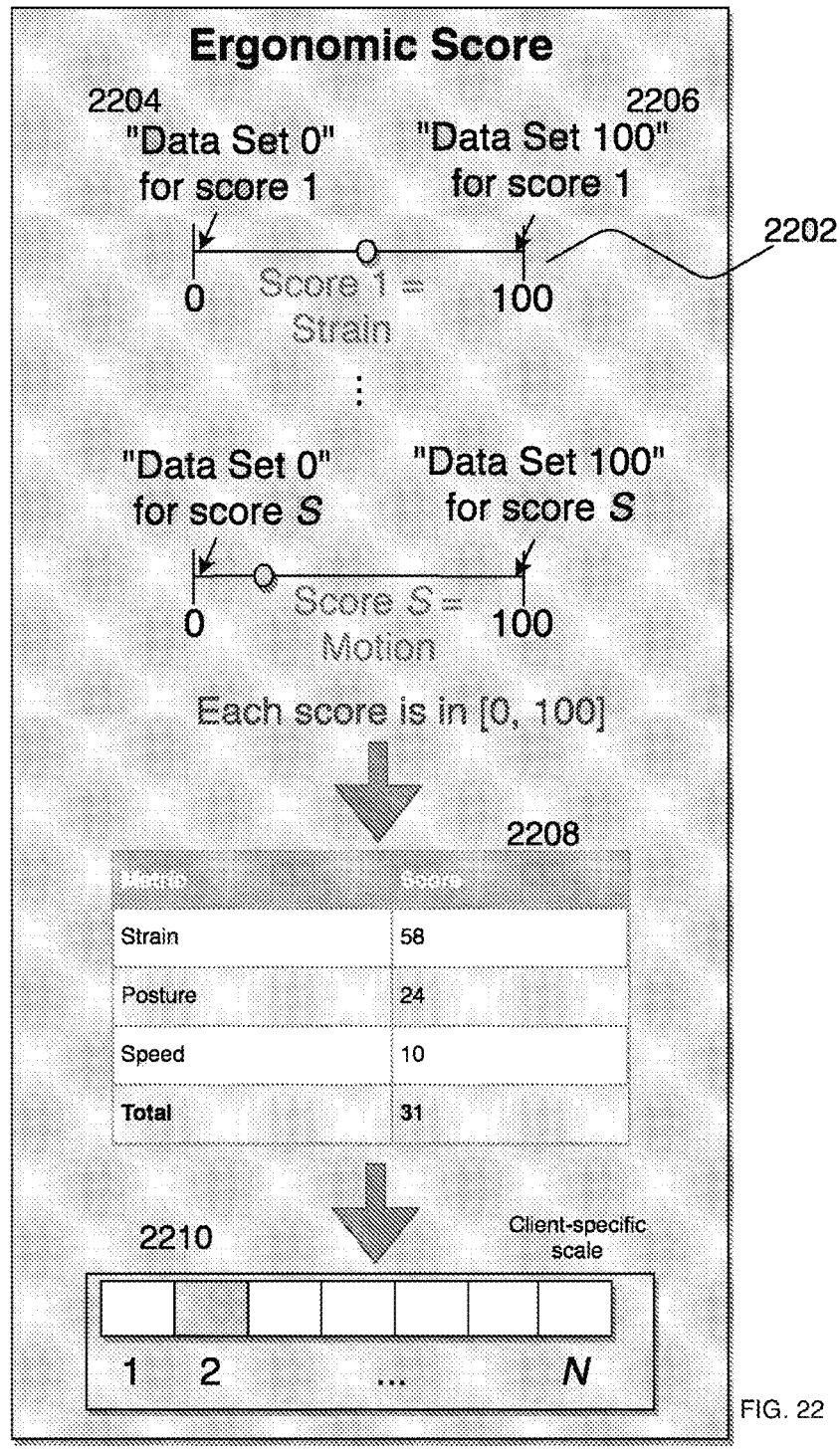
FIG. 22. is a chart illustrating the logical flow associated with ergonomic scoring carried out by the analytics platform of FIG. 13, in accordance with an embodiment of the present invention.

FIG. 22. is a chart illustrating the logical flow associated with ergonomic scoring carried out by the analytics platform of FIG. 13, in accordance with an embodiment of the present invention. Each score in FIG. 22 is defined on a common, arbitrarily chosen, scale of 0 to 100 at first 2202. These scale end-points are defined by a pre-collected set of (calibration) data. In other words, data is collected to represent a score of 0 for strain 2204 (e.g., by holding hand and wrist at zero degrees relative angle)—which is decided by an ergonomic expert and/or determined empirically. Similarly, data is collected which represents a score with the value of 100, or in other words, the most unergonomic motion practically experienced for that task. Typically, the dataset representing "Data Set 0" 2204 is a slower way to perform the worker's task but also involves being cognizant about angular deviations as explained in FIG. 24. Similarly, "Data Set 100" 2206 can be a fast way to perform the same task not being aware or caring about angular deflections between wrist and hand. The same is true for the other scores and this is what enables a common scale to be used. Then the scores are summarized to a "total score" 2208. Finally, the scores can be brought to any scale 1-N desired 2210 (specifically, such as 0-7 which resembles the RULA method scoring scale, which is an input to the scoring functionality from the user) by a simple mathematical transformation (e.g., transform a number from $x_1$-$x_2$ to another range $y_1$-$y_2$).

FIG. 23 illustrates in more detail than FIG. 22 the ergonomic scores computed to decide how ergonomic a motion is and the combination to provide the safety score, in accordance with an embodiment of the present invention. For computing the scores, a chunk of structured data is received 2302 from the data filtering pipeline 1800, FIG. 18 shows more details on the pipeline in embodiments of the present invention. In the embodiment of FIG. 23, three scores are computed: The activity score 2304, the posture score 2314, and the strain score 2320. For the activity score, a window 2306 slides over the data and takes the difference between the peak values 2308 in either direction as shown with red circles. Then, this difference is divided by the window size 2310. The value is put in a bin. The bins range from 0 through 20 (empirically determined but can be changed). The window is moved and a new count is put in its respective bin, etc. Finally, a custom weighing function can be applied to compute a final score 2312 from the bins 2330. Another score computed on the same chunk of data is the posture score 2314. This score quantifies the percentage time spent beyond a given threshold angular value 2316. The final score is the strain score 2320 which bins the angles into incremental bins of d degree ranges 2322. For example, d can be 15, then we bin the angles from 0-15, 15-30, etc. Having the bins computed a weighing function can be applied to produce a score. Finally, all three scores can be combined to a safety score 2332. In embodiments, this combination can involve taking the average of the three scores 2334, taking the maximum of them, or some other custom user-defined function.

Figure 25:
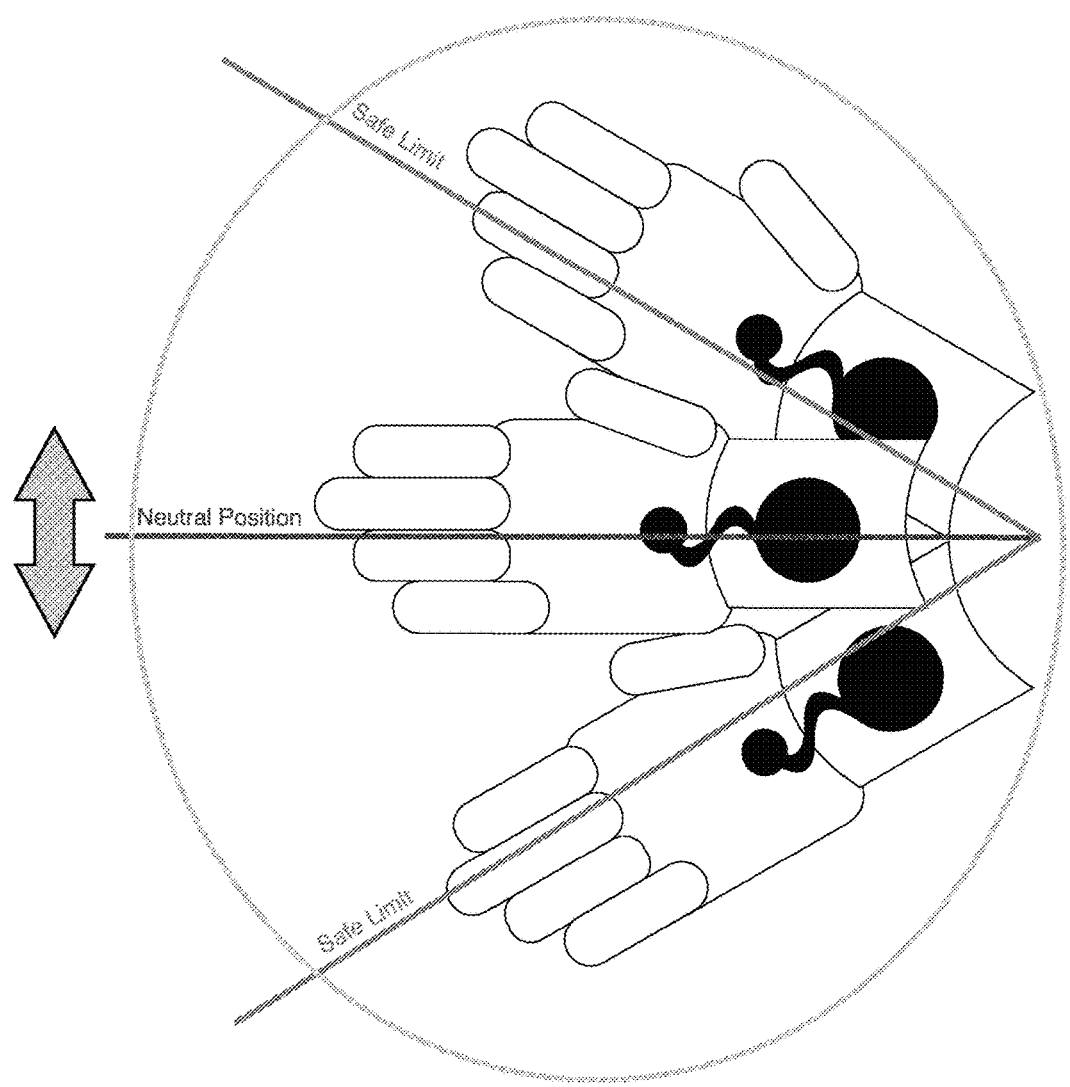
FIG. 25 illustrates safe limits associated with wrist motion.
Figure 26:
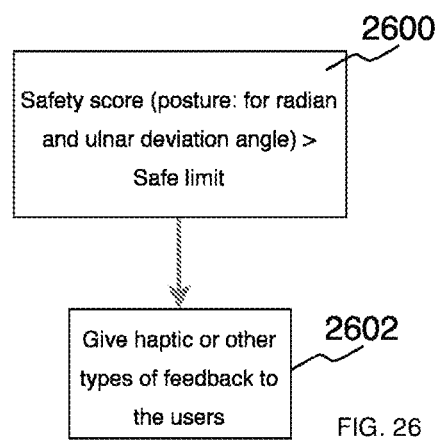
FIG. 26 illustrates a condition for providing haptic feedback, in accordance with an embodiment of the present invention.

FIGS. 24-26 show a use case of ergonomically scoring hand movements of a subject, in accordance with an embodiment of the present invention. In this use case, a wearable device is mounted across the wrist joint of a subject, as shown in FIG. 7, to measure the subject's hand posture safety during a work process.

FIG. 24 illustrates types of wrist motions used in the ergonomic scoring, in accordance with an embodiment of the present invention.

FIG. 25 illustrates safe limits associated with wrist motion. These safe limits can be applied to any of the wrist motions shown in FIG. 24. The safe limits can be modified by the user through the user interface and automatically be propagated throughout the analytics platform.

FIG. 26 illustrates a condition for providing haptic feedback, in accordance with an embodiment of the present invention. In FIG. 26, first process 2600 checks if the safety score for a parameter of the wrist motion, such as radian and ulnar deviation angle, is above a safe limit, as shown in FIG. 25. Here, to serve as an example and to simplify the discussion, it is assumed that safety score is computed only from the posture score (which the user can indeed select to always have done if posture is only relevant to the application at hand) 2314 of FIG. 23. One way to mathematically think of this is to set all weights to 0 except the weight for posture score which is set to 100% in FIG. 23, 2334. If the safety score is above the safe limit, the second process 2602 transmits, to a computing device of the subject, a physical feedback such as, but not limited to, sound, light, vibration or haptic feedback to help the subject recognize and correct the unsafe posture. To be sure, the haptic feedback can be given also when the safety score is more general, e.g., not just as computed from posture, reaches above a given threshold. The computation needed for the process 2600, 2602 can be done on the wearable itself and/or a server. The feedback may be in the form of a report generated via the server communicatively coupled to the subject's wearable device. The report on feedback may also be transmitted to the subject or subject's manager either in real-time or after the work is completed as part of a work-force summary to help determine the nature of risk and actionable items to correct the risk.

Figure 27:
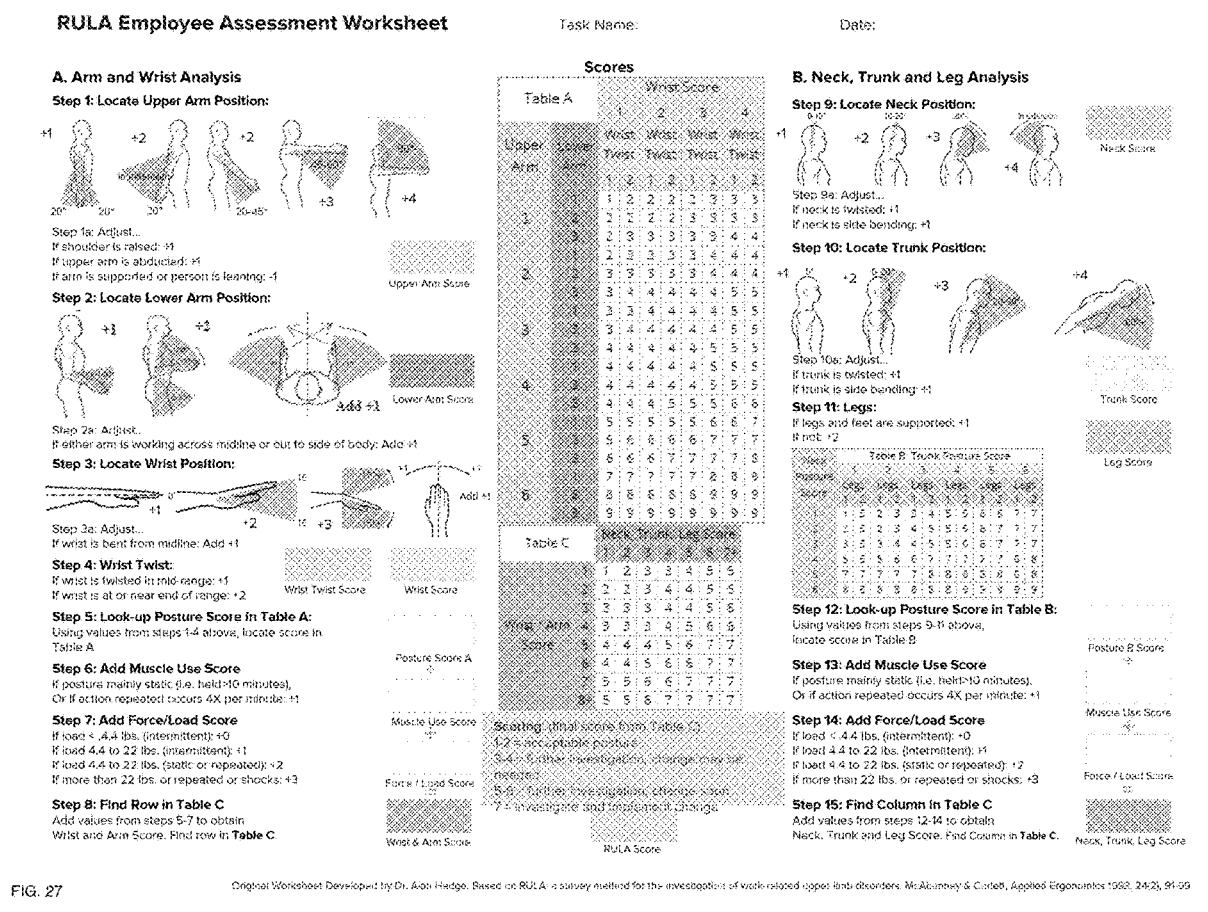

FIG. 27 shows the rapid upper limb assessment (RULA) method used to calculate an ergonomic score, in accordance with prior art. RULA is an assessment technique used to understand risk of the upper extremities, the neck, the body trunk, and legs when performing a work motion or task. RULA has several steps to assess an individual's risk. Each step contributes to the overall score associated with a safety process. Any portion of RULA can be used to develop an understanding and relative score of a portion of the body covered in the assessment. The first step is to understand the position of the upper arm while the individual is working or performing a task. The further the arm position is located from a neutral position, the higher the resulting score contribution to the RULA score. A sub-step of step 1 is to add or subtract additional components to the upper arm score if the shoulder is raised, if the upper arm is abducted, or if the arm is supported or the person is leaning.

The second step is to evaluate the lower arm position. Depending on the movement of the lower arm, and if work is done in front of the body or to the sides, as well as if the arm is raised or lowered will influence the score of this portion of the RULA. A sub-step of step 2 is to assess if the arm is crossing the midline or out to the side of the body, and if it is, an additional point would be added to the score. The third step is evaluating the wrist position. The further the range of the flexion and extension of the wrist, the higher the score is for this portion of RULA. A sub-step of step 3 is if the wrist bends from the midline (ulnar/radial deviation), add an additional point to the score.

The fourth step is evaluating if the wrist twists (pronation/supination) during the work motion or task. The further the extent of the wrist twisting the higher the score for this portion of the RULA. In the fifth step we refer to Table A, to find the total score from steps 1-4. For example, if we had a score of 2 for Step 1, we identify the corresponding row. If our score was a 3 for the lower arm score, we then identify the corresponding row within the upper arm score that identifies the lower arm score. Next, we move within our lower arm score row, to find the corresponding wrist score (step 3) column that we measured. Last, we would identify the appropriate sub-column within the wrist score, to the corresponding column for wrist twist score. This number is our posture score for the first portion of RULA. Step 6 of RULA assesses muscle activity to the movement. If during a work motion or task the individual maintains a static posture for more than 10 minutes (ex: holding arm outward in front continuously) or if the work task or motion is repeated four times or more per minute, an additional point is added to the RULA score.

The seventh step evaluates the force or load applied during the work motion or task. The force or load cannot be assessed with the current invention and so this portion of the RULA is skipped over. The eight step is to calculate the total wrist and arm score for a worker. The score determined in step 5 is to be added to the scores from step 6 and step 7. The second portion of RULA, is used to assess the neck, trunk and legs of the body. The ninth step evaluates neck position. The further the neck is bent forward or backward the higher the score is for this step. A sub-step of step 9 adds additional points to the score if the neck is twisted or the side is bent. The tenth step is to evaluate the position of the trunk. The further the trunk is bent forward the higher the score associated with this step is. For example if a worker is bent forward 30 degrees during a work task, an additional 3 would be added to the RULA score. A sub-step of step 10 is to assess if the trunk is twisted, and if the trunk bends sideward during the work motion or task. If the answer is yes, additional points are added.

The eleventh step is to assess the position of the legs. If legs and feet are supported (resting firmly on the ground) the score is one, however if the legs are not supported and one or the other is off the ground, the score here is two. Step 12 is to use the Table B provided to determine the total neck, trunk, and leg posture score. In step 12, first determine the row for the neck posture score (step 9). Once the appropriate row is found, now find the appropriate column that matches with the trunk posture score determined in step 10. One this appropriate column is found, now find the appropriate column for the leg score that is within the trunk posture score column and the neck posture score row. The number you land on is the score total for steps 9-11. The thirteenth step evaluates the use of muscles for the neck, trunk, and legs. If the posture is held statically for greater than 10 minutes, or if the action is repeated four times or more per minute, an additional point is added to the score here. The fourteenth step assesses how much force or load is applied during the work motion or task. The force or load cannot be assessed with the current invention and so this portion of the RULA is skipped over.

The fifteenth and final step sums up the scores from steps 12-14. After the score is totaled, Table C is used to get a final total RULA score. The row for the score for the wrist and arm is identified first (step 8 score). Next the column is identified for the total neck, trunk, and leg score, and matched within the row for wrist and arm score. The final score that is landed on is between 1-7 and determines the severity of the work motion or task. A score of 1-2 means that it is an acceptable posture. A score of 3-4 means that further investigation is required and that change may be needed. A score of 5-6 means that further investigation is required and that change is needed soon. A score of a 7 means that investigation is required and a change needs to be implemented immediately.

In embodiments of the present invention, the analytic platform may evaluate the data collected by the wearable devices, using one or more of the steps of RULA, to score the motions of corresponding monitored workers.

Figure 28:
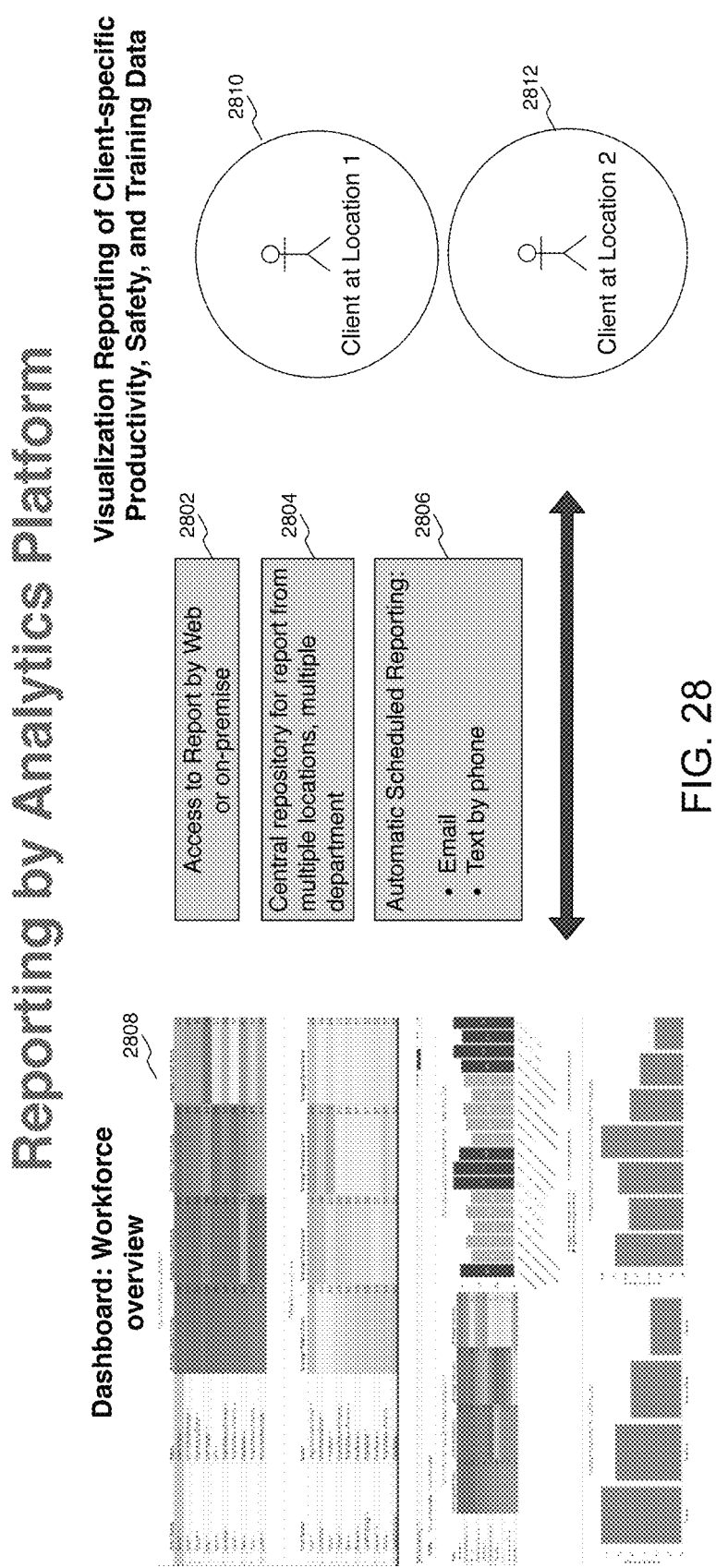
FIG. 28 provides exemplary types of reports generated by the analytics platform of FIG. 13, in accordance with an embodiment of the present invention.
Figure 30:
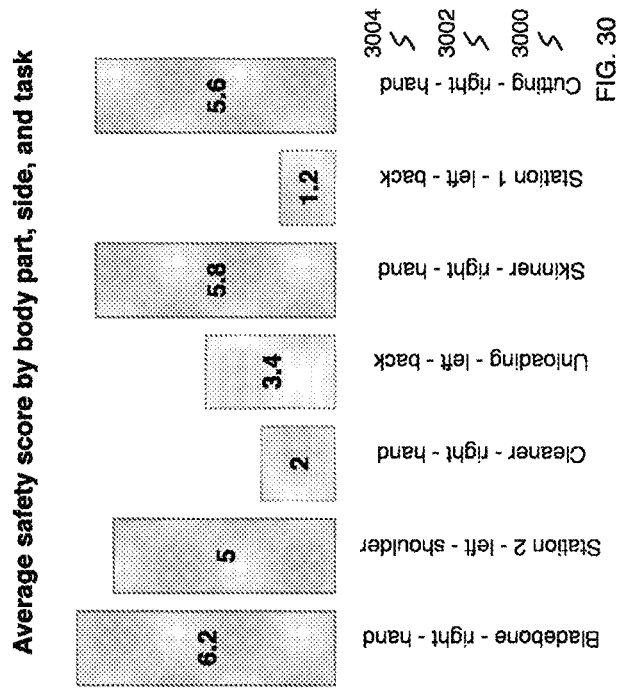

FIG. 28 provides exemplary types of reports generated by the analytics platform of FIG. 13, in accordance with an embodiment of the present invention. These sample analysis reports can also be used for associating specific worker motions to risks/injuries and their respective solutions. In the present embodiment, the analytics platform periodically computes productivity and safety scores for the workforce. These scores are populated in, e.g., an ElasticSearch database which is capable of delivering said data, and various statistics and workforce overview metrics, in a web interface 2802 which can be served locally at the client location and hence on-premise is supported as well. This includes connecting the data to, for example, Looker and/or Tableau 2808, detailed views of some example reports are shown in FIGS. 29-30. In embodiments, the client can access the report from their computers. In some embodiments the reports are stored centrally and are delivered specific to the relevant clients 2804. Some embodiments provide automatically scheduled reports 2806 delivered in any format desired. Data pertaining to training and increased productivity and safety is thus delivered to clients (client 1 potentially being an entirely separate company than client 2) of the present platform 2810, 2812.

FIGS. 29-30 provide exemplary types of reports generated by the analytics platform of FIG. 13, in accordance with an embodiment of the present invention. The analytics platform 1316 of FIG. 13 includes a Dashboard which provides an overview of the ergonomic metrics analysis of the subjects (workers) of an employer. The Dashboard provides reports on different aspects of the productivity and ergonomic analysis of a subject or group of subjects. FIG. 29 shows an ergonomics table provides a concise overview of the safety score 2902 and its breakdown 2904 across the top 10 most at-risk jobs at the client site 2900. A similar table can be constructed for the productivity and thus list the top 10 jobs being most likely to carry the highest drop in productivity during the working day. FIG. 30 demonstrates a break-down again from an ergonomic perspective of the job 3000 but also now by worker hand (right or left) 3002 and body-joint part (hand, shoulder, etc.) 3004. Actionable insights can come from the client defining a tolerance on the scores and taking action such as re-training that specific job or making changes to the shifts and/or workstation setup, to name a few.

Figure 31:

FIGS. 31-32 show example reports provided, by the analytics platform of FIG. 13, to a mobile computing device of a subject on the subject's monitored performance, in accordance with an embodiment of the present invention. The report of FIG. 31 is in the form of a text/multi-media message sent to the subject to encourage performance and improve safety of the subject. The report of FIG. 32, also covered in FIG. 28, can be sent to the subject and/or subject's manager where more summarized information is sent to the subject's phone as shown in FIG. 31.

Figure 33:
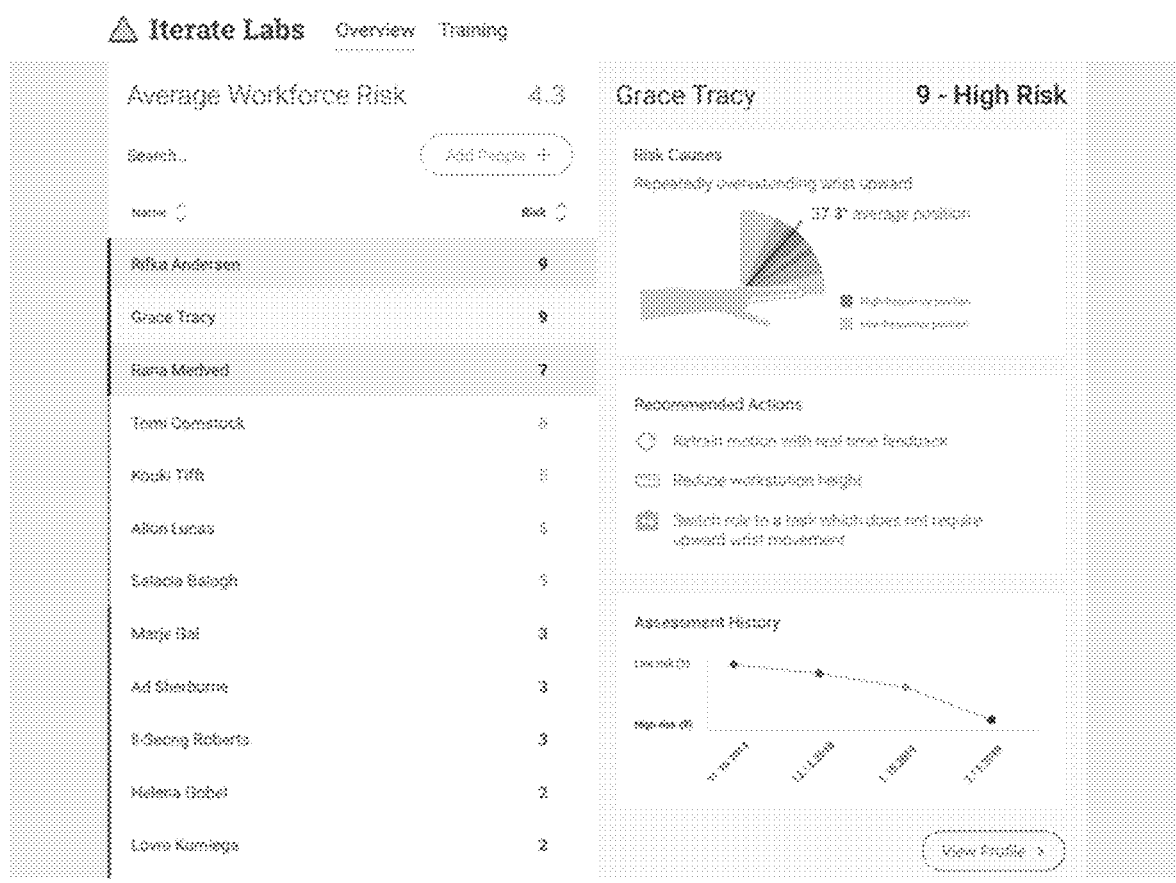
FIGS. 33-34 show exemplary reports provided, by the analytics platform of FIG. 13, to a supervisor on a subjects' monitored performance, in accordance with an embodiment of the present invention
Figure 34:
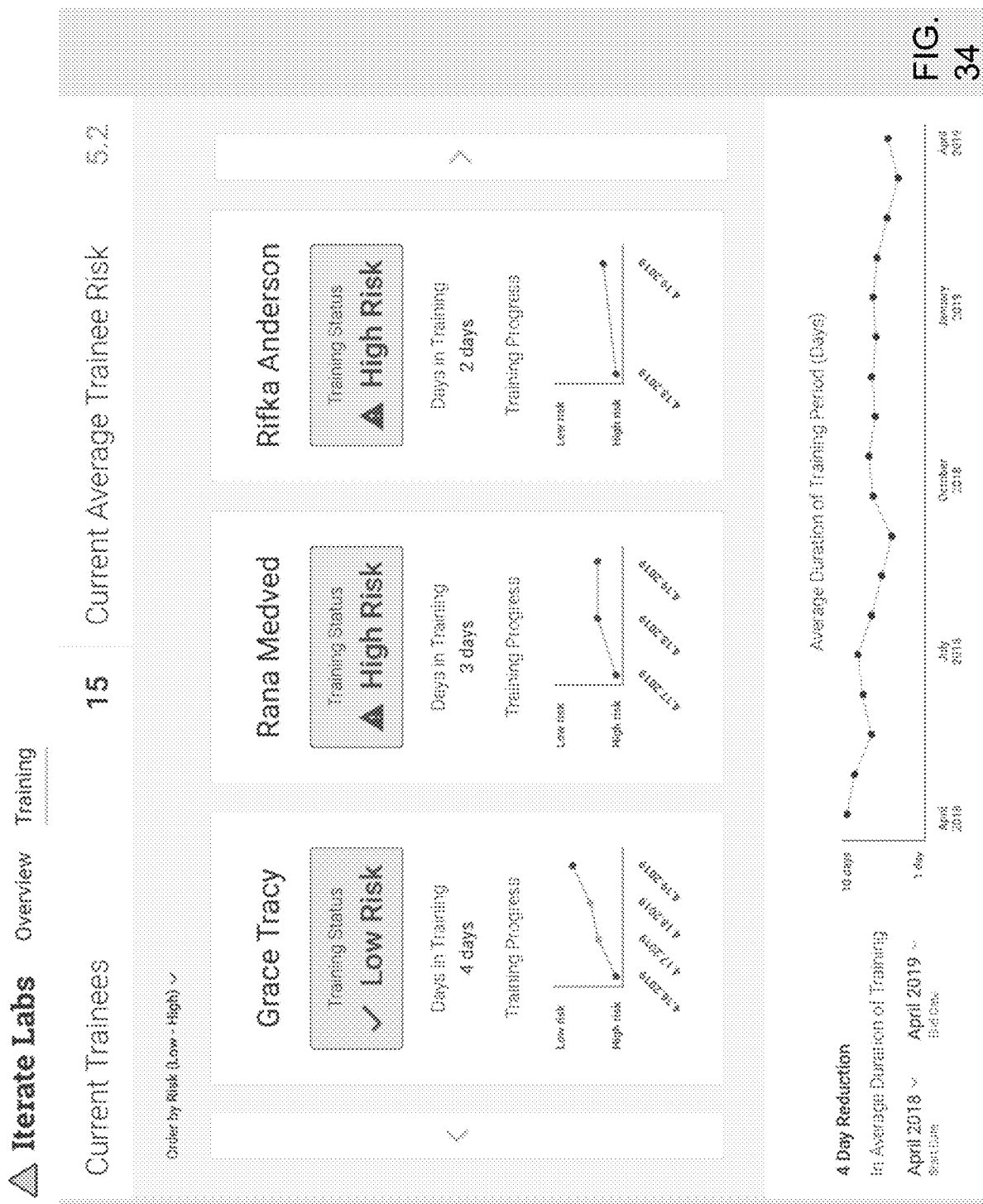

FIGS. 33-34 show exemplary reports provided, by the analytics platform of FIG. 13, to a supervisor on a subjects' monitored performance, in accordance with an embodiment of the present invention. The reports include the risk scores of the subjects. The reports of FIGS. 33-34 are generated based on the subjects' work and posture to summarize the subjects' safety, fatigue, and productivity. These reports may also include actionable items for managers/supervisors to use to help work safety and productivity of the subjects.

Figure 35:
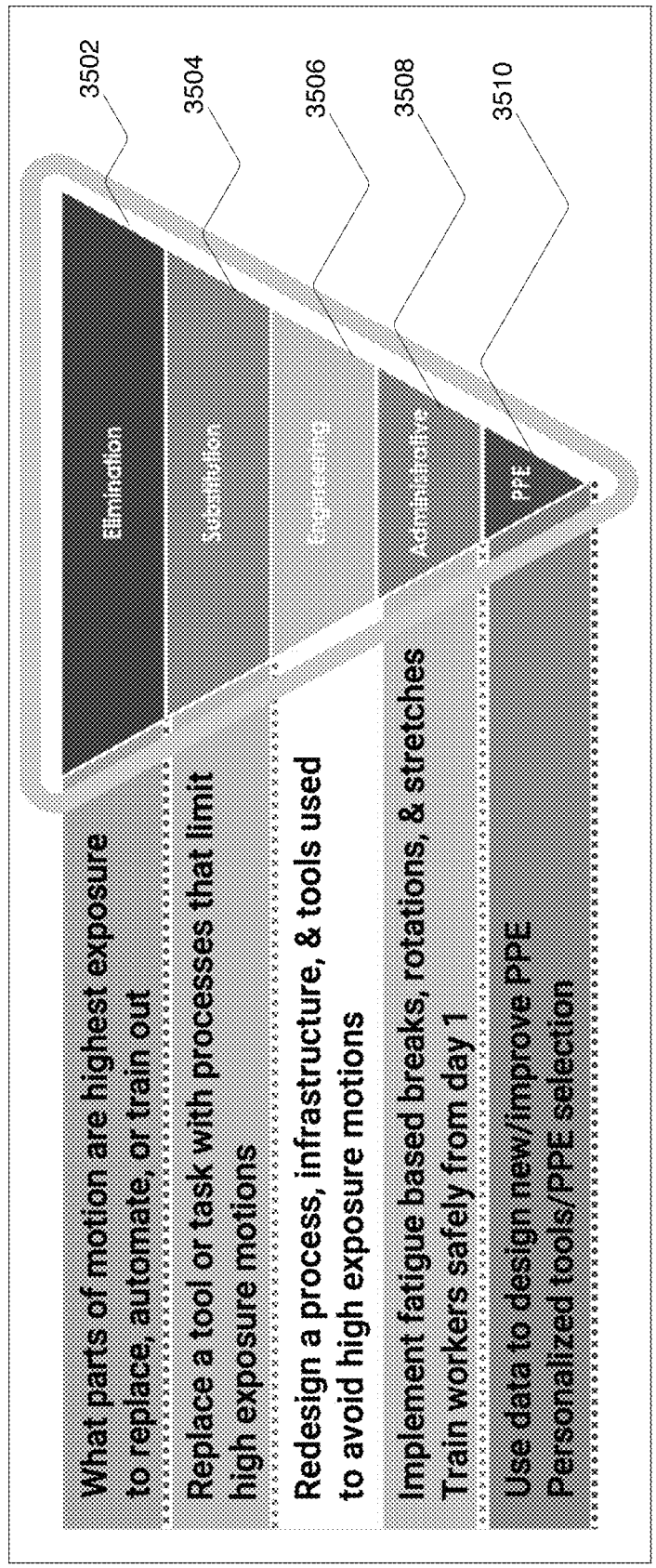
FIG. 35 shows how the analytic platform of FIG. 13 aligns safety management practices to the OSHA hierarchy of control, in accordance with an embodiment of the present invention.

FIG. 35 shows how the analytic platform of FIG. 13 aligns the safety management practice to OSHA hierarchy of control, in accordance with an embodiment of the present invention. The chart of FIG. 35 shows how the motion data collected from the wearable devices may cause change and providing insights to each level of the OSHA Hierarchy of Controls. First, the data may be used with respect to the "Elimination" step 3502. The "Elimination" step pertains to physically removing an associated hazard from the work environment. Here, data may be informative of what parts of a motion or task of a worker are most unsafe and require the motion or sub-part of a motion to be replaced with a safer path, to be automated out, or to train away the motion. A safety score or other related metric derived from the data may be used to identify what portions of a work task are the highest risk motions for a worker to perform. For example, if, using the motion data, the portion of a task in which a worker is turning a handle is calculated to have a high posture score, the turning of the handle portion of the task would need to be eliminated. In this example, the data would show that for the remainder of the task the worker has a low posture score, but for the one segment in which the handle is turned the posture score is elevated. A variety of scores may indicate that a task is unsafe, such as a posture score, a speed score, a fatigue score, or other related safety metric. Matching a specific work motion, with a large database or catalog of work motions (such as provided via the analytics platform of the present invention) may be used to identify the work motion causing an issue. Such determination of a specific cycle of a work task or process, can aid in the ability to identify a specific portion of a task where a safety score is elevated.

Second, the data may be used with respect to the "Substitution" step 3504. The "Substitution" step pertains to replacing material or a process with another material or process that is considered to be less of a hazard. Here, the motion data collected by the wearable device may be informative of how and if a tool or task can be substituted out for a tool or task that limits the unsafe motions occurring. For example, in a process where a worker picks up a tool, engages with a product, and then picks up the product, there may we many different approaches to perform that overall task, or any of those sub-tasks. In embodiments, alternative approaches, movements, positioning, or tools can be used to perform the same task and sub-tasks, and then measure if the elevated safety score has been reduced to one in a safe operating level. If an alternative approach is performed that eliminates the unsafe motion, the new approach may be substituted for the way it was previously performed.

Third, the data may be used with respect to the "Engineering" step 3506. The "Engineering" step pertains to the use of engineering controls to isolate a worker from a hazard or to place a barrier between the worker and the hazard. Here, the motion data collected by the wearable device may be informative of how to best redesign a process, current or future infrastructure, or tools used to best limit and avoid unsafe motions.

Fourth, the data may be used with respect to the "Administrative" step 3508. The "Administrative" step pertain to changing the methods and habits of a worker, with the end goal to limit the exposure of the worker to the hazard. Here, the motion data collected from the wearable device may be used to inform modifications and enforcement of breaks, rotations, and stretches that follow best practices to avoid musculoskeletal injuries. For example, if fatigue is detected in a worker due to low level of productivity scores and/or prolonged high safety scores, an alert may be sent, via the analytics platform, to workers and or management to trigger a break, rotation, or stretch to occur. The break, rotation, or stretch may be then be monitored through further motion data, collected via the wearable device, to ensure that it was taken by the worker, to ensure the appropriate stretches occurred, and to ensure that the rotation to the appropriate workstation occurred. Breaks, rotations, and stretches may also be optimized based on exposure levels and fatigue levels indicated by the collected data. The collected data and the overall analytics platform infrastructure can be used to help train workers on how to safely and productively move and operate in a facility from the first day they are hired.

Data collected by workers' wearable devices during the train phase can be used to understand if each worker is performing the task in an appropriate manner. An initial database of workers performing the task in an ideal fashion can be built to compare to the data collected by the wearable devices during the training phase. This collected data can be evaluated, by the analytics platform for safety scores, productivity scores, fatigue levels, and other relevant metrics to assess the ability of a trainee. The data collected by the wearable devices are useful in screening the correct candidates for a task or job. The previously collected data from a large pool of workers will indicate the appropriate biomechanics one must possess to perform the task effectively.

Fifth, the data may be used with respect to the "Personal Protective Equipment (PPE)" step 3510. The "Personal Protective Equipment" step pertains to ensuring that workers are equipped with the appropriate personal protective equipment (gloves, hard hats, clothing) to protect from exposure to a hazard. Here, the data collected by the wearable devices may be used in determining the design of new PPE, improved PPE, or the personalized matching of PPE to a worker's biomechanics. For example, if the data collected on a worker demonstrates, via the analytics platform, a worker has a high posture score when holding a specific tool, a tool with a modified grip to account for poor posture may be used instead. The individual's biomechanics and physical attributes may influence how the individual interacts within their work environment, and thus different tools or PPE may be appropriate. The data collected by the wearable device may highlight specific exposures that are created as a result of the current tool or PPE design, and identify changes that will help eliminate unsafe motions. The data may also be used to help facilitate the personalization of tools for individual worker biomechanics.

Figure 36:
FIG. 36 illustrates how the wearable of FIG. 1 and the associated analytic platform of FIG. 13 can drive safety management across multiple facilities located in different parts of a country, in accordance with an embodiment of the present invention.

FIG. 36 illustrates how the wearable device of FIG. 1 and the associated analytics platform of FIG. 13 can drive safety, productivity, and operational management across multiple facilities located in different parts of a country, in accordance with an embodiment of the present invention. In embodiments, data collected by the wearable device can be informative of where certain strengths and weaknesses in safety, productivity, operations, training, and other areas lie across a corporation. In some embodiments, data collected via the wearable device of workers at a facility is aggregated, via the analytics platform, to get an average or overall safety, productivity, or other related score. The scores may be aggregated on a facility level, or across the entire organization to understand the average score for an organization. The score may be presented on a daily basis, or any longitudinal basis. In some embodiments, the scores calculated per facility are compared to other facilities across a single organization. The scores may be evaluated to historical scores to evaluate performance over time. For example, if two facilities have very similar overall processes, the average or overall safety score may be used to broadly assess safety performance between the two facilities. Comparison of safety scores can be made across as many facilities as an organization has, so as to best understand where safety, productivity, or other areas of concern may be. The data can be used to evaluate the effectiveness of training by aggregating the safety and productivity scores for a facility and comparing it to another comparable facility within an organization.

In some embodiments, the data collected by the wearable devices is used to understand operations by evaluating the levels of fatigue, productivity, and safety across a facility and comparing it to other facilities. For example, the number of breaks or rotations scheduled for workers compared to the actual numbers of breaks and rotations taken by the workers may be a measure of operational performance. Another measure of operational performance may be the total amount of time that workers are moving compared to the total amount of time where workers are not moving. In some embodiments, the data is also aggregated, by the analytic platform, on different levels throughout the organization to make comparisons, such as a specific processing line, a specific type of work, or other categories that define a worker within an organization. The comparison may be used to understand differences (safety, productivity, fatigue) between the same process at two different facilities. For example, if a worker operates on processing line A in facility A, and it is desired to compare performance of processing line A in facility A to processing line A in facility B, the two data sets and the relevant scores can be used to compare the processes at each facility.

In some embodiments, the data is used for the design and implementation of best practices across multiple facilities, monitoring of the changes, and standardization of practices across facilities. For example, if as part of a new best practices standard, a new piece of personal protective equipment were implemented, or a specific part of a task was automated across all facilities within an organization, the data may be used to understand how the new standardization impacted worker scores across facilities, and if all facilities implemented the new standards appropriately. In this way, the data can inform across a corporation where to best devote resources to improve worker worker's safety practices. For example, if evaluating the data from all the facilities across an organization, one of the assessed locations has the highest safety score, and the single highest safety score for a processing line, additional safety team members and attention would be devoted towards that facility and line. After a change is implemented, it may then be monitored using the data collected from the wearable devices and the analytics platform.

Figure 37:
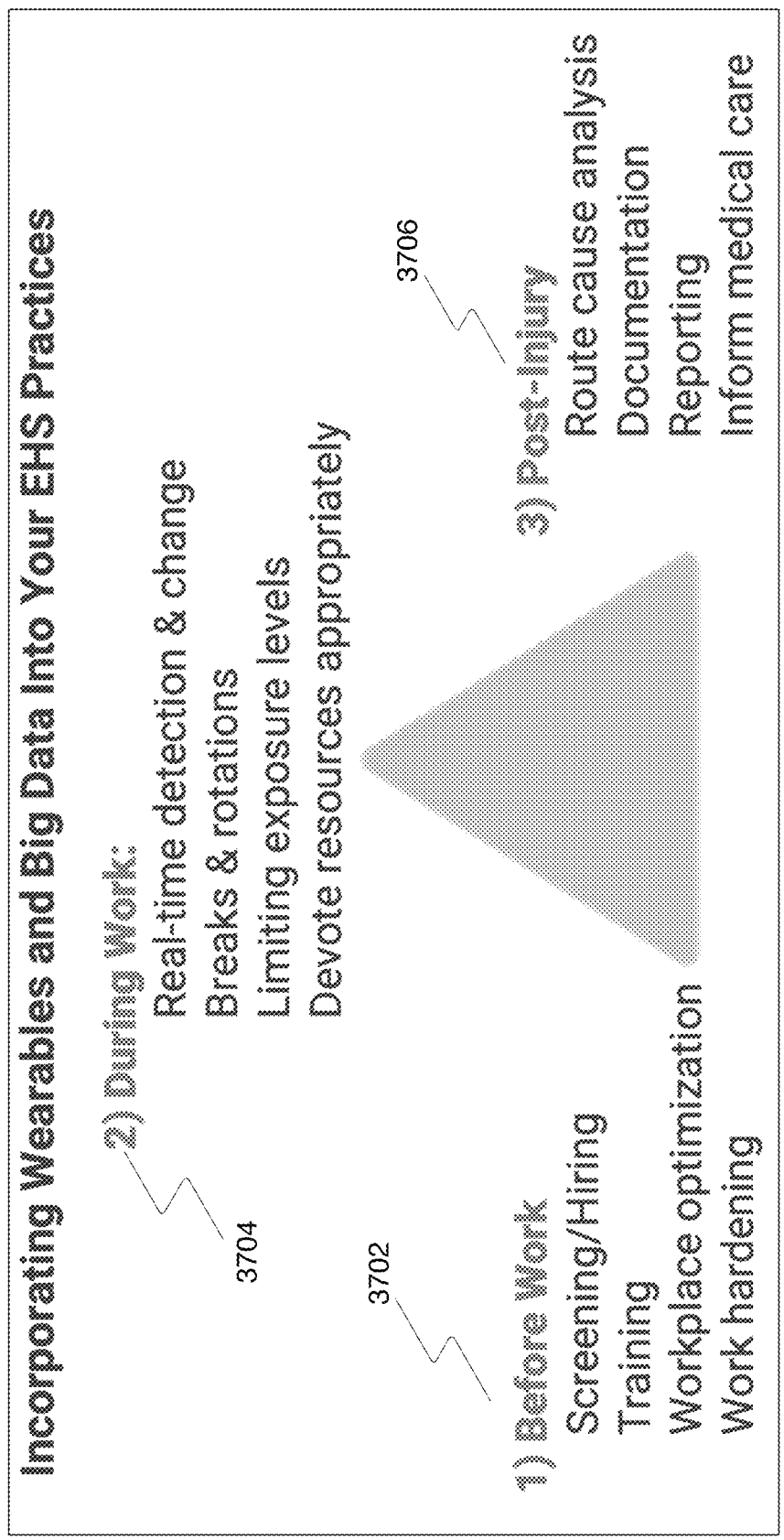
FIG. 37 illustrates how the wearable of FIG. 1 and the associated analytics platform of FIG. 13 can be incorporated into a company's Environmental Health Safety (EHS) practices, in accordance with an embodiment of the present invention.

FIG. 37 illustrates how the wearable of FIG. 1 and the associated analytics platform of FIG. 13 can be incorporated into a company's Environmental Health Safety (EHS) practices, in accordance with an embodiment of the present invention. Such data may be used towards improving an organizations safety and health practices at many stages: (i) before a worker is hired 3702, (ii) during work after a worker is hired 3704, and (ii) after an injury has occurred 3706. First, the data and wearable platform may be used to optimize and inform safety practices before a worker is hired 3702 and immediately after. For example, the data and platform may be used to evaluate candidates during a screening and hiring process, to best evaluate a candidate's biomechanics and ability to withstand the exposures they will experience during work. For another example, the data and platform may be used to optimize the workstation that a worker will be using immediately after they are hired. This can involve mapping out the working area, the exposures the worker will experience on a daily basis based on their biomechanics, and using the platform to monitor the improvements made. For a further example the data and platform may be used to monitor and improve the work hardening process associated with the hiring process. Data collected can determine exposure and performance level, as well as the degree that the worker is ready to be fully deployed on to a job. The data and platform may be used immediately after a candidate is hired to aid, accelerate, and improve the training process to ensure the worker is operating safely from the start.

Second, the data and wearable platform may be used to optimize and inform safety practices once a worker is hired 3704 and has begun their normal rotation. For example, the data and platform may be used for real-time risk detection and feedback to prevent unsafe motions performed. The data and platform may also be used to alert workers of needed breaks or rotations, as well as to optimize the breaks and rotations based on exposure levels of a worker. The data and platform may also be used to monitor cumulative exposure levels of workers over various periods of time (day, week, month, etc) and alert workers or management of needed breaks or changes when that exposure level is reached. The data and platform may further be used to alert managers, operators, or others involved in operational practices where resources need to be devoted to address an exposure.

Third, the data and wearable platform may be used after an injury has occurred 3706 in the workplace. For example, the data and platform may be used to perform a root cause analysis to understand what exposures led to an injury occurring, and to specifically understand what motions, exposures, or anomalies led to the injury. A root cause analysis driven by data can help to ensure similar injuries do not occur in the future. The data and platform may also be used to determine if the exposures that occurred during the job were sufficient to lead to an injury outcome, or if the exposure levels were within safe operating conditions. The data may further be used to monitor the workers patterns over a period of time (days, weeks, months, etc.) to understand if there were trends that led to the injury outcome. The data and platform may also be used to identify if exposures outside of working hours occurred that led to the injury outcome. For example, a worker having normal exposure levels on the Friday before a weekend during which said worker will not be working, and returning to work on Monday with very different working habits, may suggest that there were exposures to the worker that occurred over the weekend that led to the worker's injury. The data and platform may further be used for additional documentation to provide specific exposures to medical professionals or others to help aid and accelerate the diagnosis or recovery process. The data and platform may also be used for reporting purposes for corporate logs.

Figure 40:
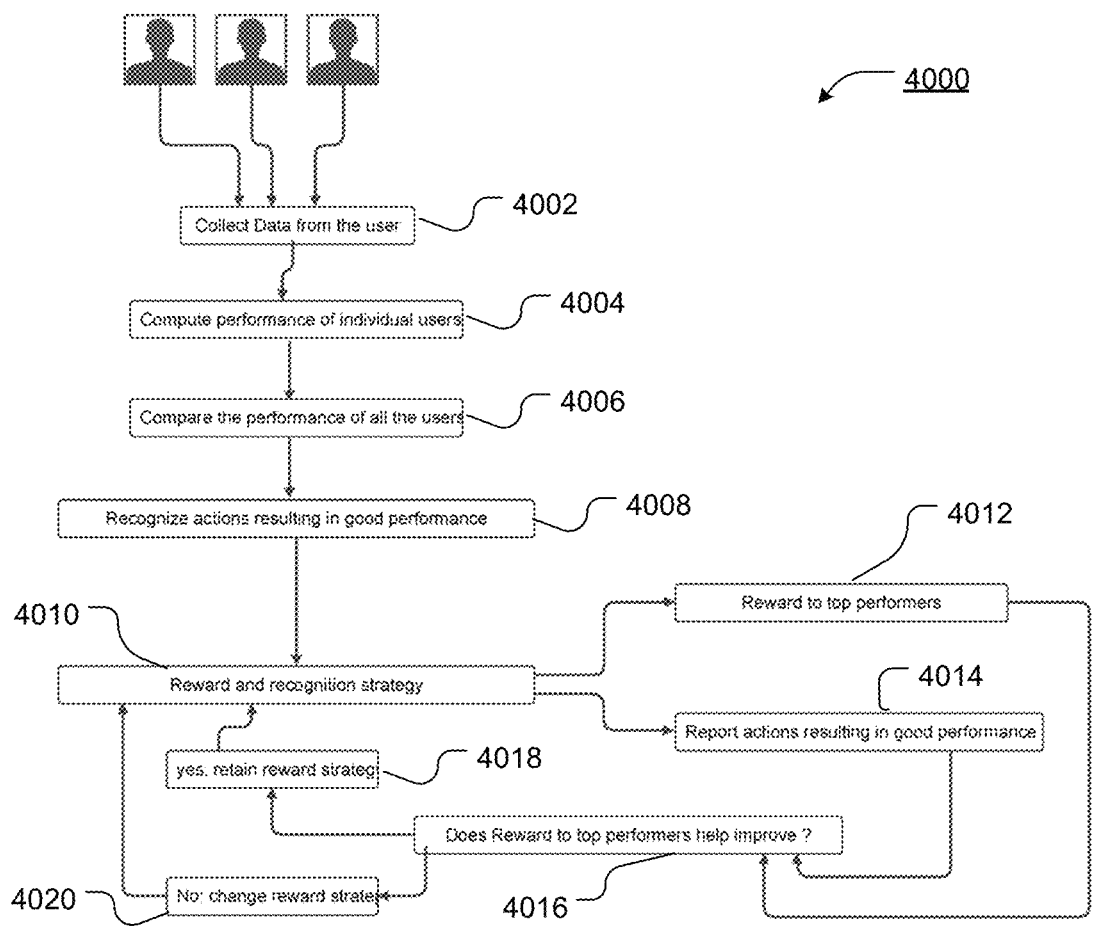
FIG. 40 is a flowchart of a process or set of processes or gamification in accordance with an embodiment of the present invention.

FIG. 40 is a flowchart of a process or set of processes 4000 for gamification. Gamification is used to engage subjects, workers, or team members emotionally and to reward team members for desirable safety and productivity. The reward may be recognition, a gift, or remuneration. The reward and recognition strategy described herein is geared towards sustaining engagement and modifying work habits.

The set of processes 4000 is executed on a server system that is coupled over a network to a plurality of network-enabled performance monitoring devices. The performance monitoring devices may, for example, correspond to the devices described in detail above in reference to FIGS. 1-5 and 38-39. Alternatively or in addition, one or more performance monitoring devices in the set of performance monitoring devices may be smart watches or similar devices. Each performance monitoring device is associated with a distinct subject.

In process 4002, the server system receives, from each member of the set of performance monitoring devices, data characterizing performance of the corresponding subject, or user. The server system receives this data over the network. The server system then processes and stores the received data. A database in the server system provides performance data, organized according to subject, which characterizes the physical performance of the corresponding subject in carrying out a work task. As part of the processing, the server system, in process 4004, computes the performance of an individual subject. In process 4006, the server system computes the performance of all subjects associated with the performance monitoring devices in the set of performance monitoring devices.

In process 4008, the server system recognizes actions resulting in good performance and further processes the performance data to develop a set of scores of each of the subjects. The set of scores may be based on the recognized actions resulting in good performance. Alternatively or in addition, the set of scores may be based on recognized actions resulting in poor performance, or it may be based on other criteria.

The server system then processes the set of scores in accordance with the reward and recognition strategy in process 4010. In process 4012, the server system assigns rewards to top performing subjects. The subjects may be personally or publicly recognized, acknowledged, and/or rewarded. The rewards can be virtual, such as points or bonus points. The rewards can also be physical, such as gifts. In addition, subjects can be rewarded with both virtual and physical rewards, such as receiving both bonus points and a gift. The recognition and rewards are geared to motivate the subjects to recognize and adopt work habits that improve work performance such as safety, productivity, etc.

In process 4014, the server system causes distribution of the set of scores to a set of recipients, for example by reporting the scores and reporting actions resulting in good performance. Exemplarily, the set of recipients may include the corresponding subject for a certain score, it may include all subjects, it may include supervisors or managers of the subjects, or combinations thereof.

The server system may also evaluate and adapt the reward and recognition strategy followed in process 4010 based on the results of the processing and based on the set of scores. In process 4016, the server system determines whether the rewards assigned in process 4012 help improve the physical performance of the subjects in carrying out the work task. If the server system determines that the rewards help improve performance, the server system retains the reward and recognition strategy in process 4018. If the server system determines that the rewards do not help improve performance, the server system may change or adapt the reward and recognition strategy in process 4020.

Figure 41:
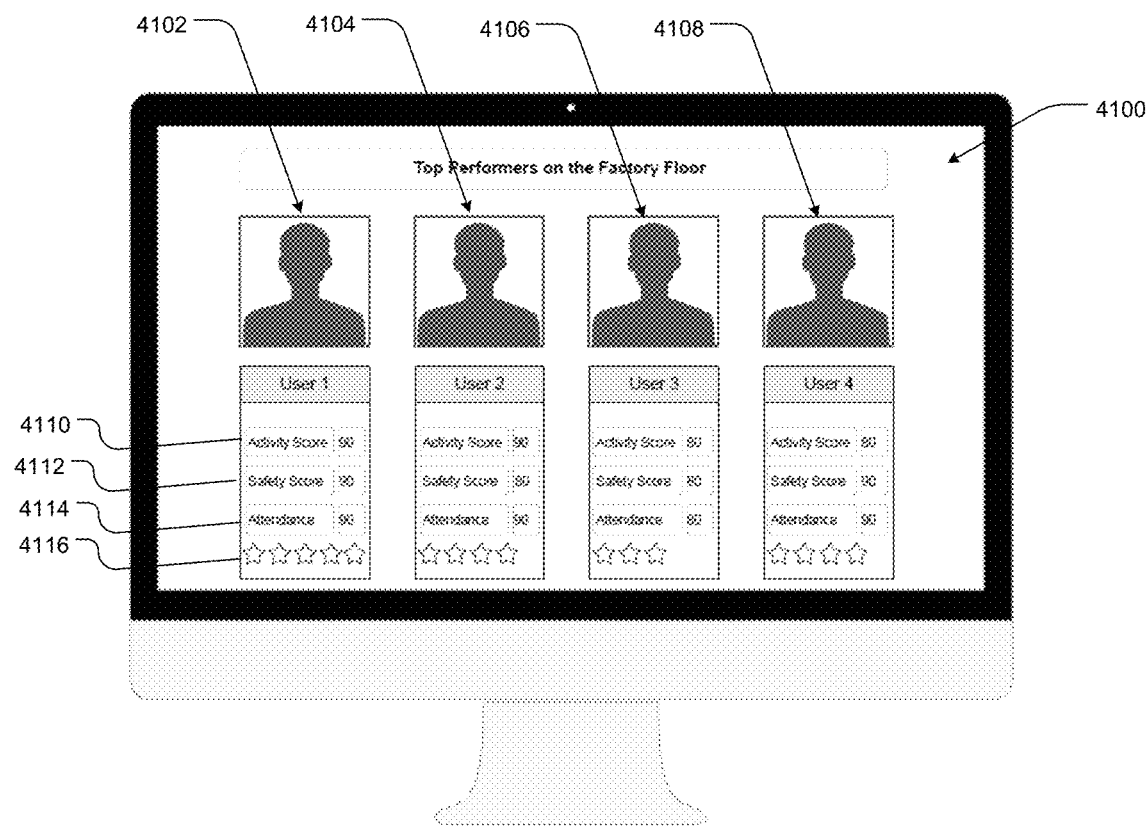
FIG. 41 illustrates an exemplary user interface for reporting and displaying a set of scores in accordance with an embodiment of the present invention.

FIG. 41 shows an exemplary user interface 4100 for reporting and displaying the set of scores computed by the server system. The user interface may be displayed by the server system, or it may be displayed by another device that receives the data from the server system. The user interface may be personal, i.e., the scores are visible to only the subject to whom the scores apply to, or it may be public, i.e., some or all scores of a subject are visible to other subjects or users of the system as well. The other users may include all subjects/workers, or they may include a subset of workers. The user interface may also be personal in that some or all scores are not visible to the subject, but only to the subject's supervisor or manager. The user interface displays scores and ratings for four exemplary users 4102, 4104, 4106, and 4108. In addition to the scores and ratings, a profile picture may be displayed for each of the users. It is further expressly contemplated that scores and ratings for a different number of users are displayed in the user interface. For example, scores may be displayed for less than four users or more than four users.

Illustratively, the user interface displays scores 4110, 4112, and 4114 for user 4102. Score 4110 may be an activity score. The activity score reflects productivity of the corresponding subject over a certain time period. Score 4112 may be a safety score. The safety score reflects safety and safe work performance of the corresponding subject over a certain time period. Score 4114 may be an attendance score. The attendance score reflects the attendance of the corresponding subject over a certain time period. While activity/productivity, safety, and attendance scores are shown, it is expressly contemplated that other scores relating to work performance are computed and displayed. Further, less than three or more than three scores may be shown.

The user interface may also display an overall rating 4116 for user 4102. Illustratively, the overall rating 4116 is a number of stars between 1 and 5, or fractions thereof. The overall rating may be computed from a weighted average of the scores 4110, 4112, 4114. The overall rating may also computed from less or other scores than the scores displayed.

Figure 42:
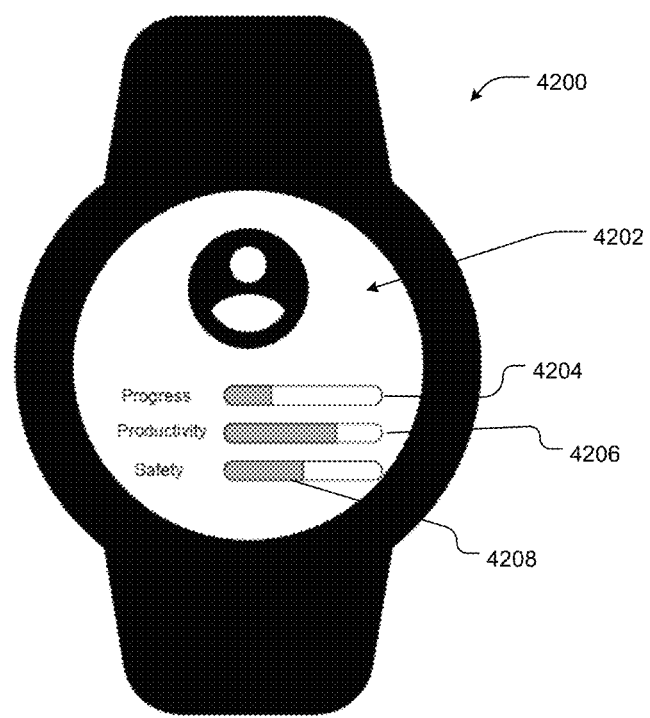
FIG. 42 shows a user interface displayed on a subject's performance monitoring device in accordance with an embodiment of the present invention.

FIG. 42 shows a user interface displayed on a subject's performance monitoring device 4200. The subject may be engaged in a current work task or in a set of work tasks. The performance monitoring device 4200 has a display displaying a user interface 4202. The user interface 4202 includes, among others, a set of scores. Illustratively, the user interface has scores 4204, 4206, and 4208. Score 4204 may be a progress score. The progress score reflects the progress of the subject towards completing a certain work task or a set of work tasks. Score 4206 may be a productivity score. The productivity score reflects the productivity of the subject for the current work task, for a set of work tasks, or over a certain time period. Score 4208 may be a safety score. The safety score reflects the safe work performance of the subject for the current work task, for a set of work tasks, or over a certain time period. Similar to what is described above with reference to FIG. 41, the set of scores shown in user interface 4202 is exemplary only.

Figures 43A, 43B:
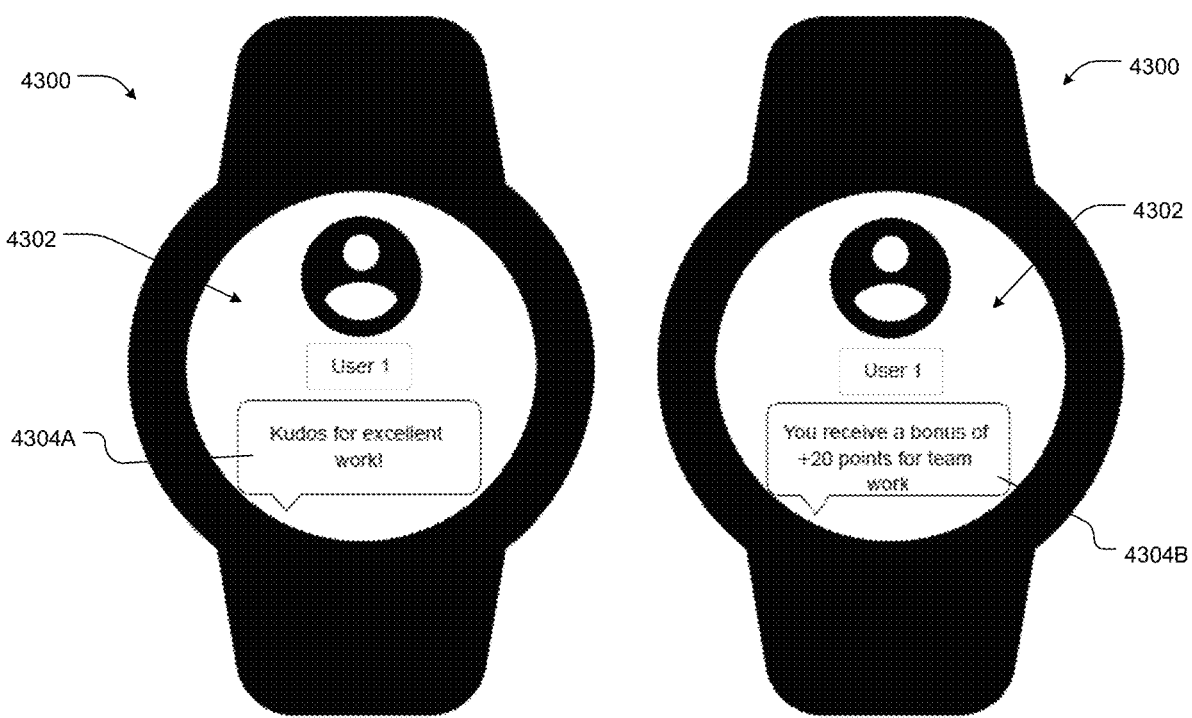
FIGS. 43A and 43B show a user interface displayed on a subject's performance monitoring device in accordance with an embodiment of the present invention.

FIGS. 43A and 43B show another embodiment of a user interface displayed on a subject's performance monitoring device 4300. User interface 4302 includes, among others, a field for a text message that is displayed to the subject. The text message may be part of the reward and recognition strategy described above. For example, text message 4304A recognizes the subject for excellent work. Text message 4304B rewards the subject with 20 bonus points for team work. The text message displayed may be selected by the server system and sent to the respective subject automatically in accordance with the organization's reward and recognition strategy. Alternatively or in addition, the text message displayed may be selected by a subject's supervisor or manager to recognize or reward work performance.

The present invention may be embodied in many different forms, including, but in no way limited to, computer program logic for use with a processor (e.g., a microprocessor, microcontroller, digital signal processor, or general purpose computer), programmable logic for use with a programmable logic device (e.g., a Field Programmable Gate Array (FPGA) or other PLD), discrete components, integrated circuitry (e.g., an Application Specific Integrated Circuit (ASIC)), or any other means including any combination thereof.

Computer program logic implementing all or part of the functionality previously described herein may be embodied in various forms, including, but in no way limited to, a source code form, a computer executable form, and various intermediate forms (e.g., forms generated by an assembler, compiler, networker, or locator.) Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies, networking technologies, and internetworking technologies. The computer program may be distributed in any form as a removable storage medium with accompanying printed or electronic documentation (e.g., shrink wrapped software or a magnetic tape), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

While the invention has been particularly shown and described with reference to specific embodiments, it will be understood by those skilled in the art that various changes in form and detail may be made therein without departing from the spirit and scope of the invention as defined by the appended clauses. While some of these embodiments have been described in the claims by process steps, an apparatus comprising a computer with associated display capable of executing the process steps in the claims below is also included in the present invention. Likewise, a computer program product including computer executable instructions for executing the process steps in the claims below and stored on a computer readable medium is included within the present invention.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A system comprising:
   a set of monitoring devices, each device being attached to a limb of the subject associated with a distinct subject performing physical tasks in connection with a set of workplace activities, and having:
   a set of assemblies, constituting a subsystem, each assembly including a housing and a set of sensors and configured for removable attachment to a body part of the subject;
   a controller, disposed in the subsystem, coupled to the sensors, and configured to perform initial processing of data from the sensors; and
   a wireless transceiver disposed in the subsystem, coupled to the controller, and configured to transmit the initially processed data to a server system; and
   a non-transitory computer readable storage medium storing a set of instructions, which, when executed by the server system, establish a set of computer processes, the computer processes comprising:
   receiving by the server system, over the network, from each member of the set of monitoring devices, data characterizing performance of the corresponding subject;
   processing and storing the received data to provide, in a database, performance data, organized according to subject, characterizing physical performance of the corresponding subject in carrying out the set of workplace activities;
   further processing the performance data to develop for each subject an ergonomic score for a set of ergonomic metrics based on a predefined ergonomic assessment method, to quantify motions that are unproductive and suboptimal; and
   causing distribution of the-ergonomic score for each subject to a set of recipients.

2. A system according to claim 1, wherein the set of sensors is selected from the group consisting of an accelerometer, a gyroscope, a magnetometer, a thermistor, an EMG sensor, and combinations thereof.

3. A system according to claim 1, wherein the processing of the data includes cleaning the data.

4. A system according to claim 3, wherein the data is cleaned using a technique selected from the group consisting of clustering, principal component analysis (PCA), mean mesh (MM) PCA, data imputation, time stabilization, standard deviation of time, temporal-angular filter, and combinations thereof.

5. A system according to claim 1, wherein the processing of the data includes computing ergonomic metrics on the data.

6. A system according to claim 1, wherein the ergonomic metrics are selected from the group consisting of strain, posture, speed, differential angle, and combinations thereof.

7. A system according to claim 1, wherein the ergonomic scoring is based on a measurement of relative angular motion about a joint using a measure selected from the group consisting of radial angle, ulnar angle, flexion angle, extension angle, pronation angle, supination angle, and combinations thereof.

8. A system according to claim 1, wherein the ergonomic scoring is calculated using an assessment method selected from the group consisting of RULA scores, Moore Garg Strain Index, American Conference of Governmental Industrial Hygienists (ACGIH) Hand Activity Level, Assessment of Repetitive Task (ART), Iterate Lab scores, and combinations thereof.

9. A system according to claim 1, wherein the ergonomic scoring is based on a parameter, relating to the relative motion, the parameter measuring an extent to which the relative motion has exceeded a pre-defined safe limit, and selected from the group consisting of intensity, duty cycle, frequency, and combinations thereof.

10. A system according to claim 1, wherein the processing of the performance data includes employing machine learning techniques to assess data associated with repetitive physical tasks performed by the subject.

11. A system according to claim 1, wherein the processing of the performance data includes generating a report based on the data and transmitting the report to a computing device of a user.

12. A system according to claim 1, wherein the processing of the performance data includes generating an alert based on the data and transmitting the alert to a computing device of the user.

13. A system according to claim 1, wherein the server system has been configured to generate reports and alerts based on the processed ergonomic performance data.

14. A system according to claim 1, wherein the processing of the performance data includes determining parameters applicable to performing tasks associated with a lean manufacturing methodology, the methodology selected from the group consisting of standard work, labor standards, and combinations thereof, such parameters selected from the group consisting of cycle time, cycle count, uptime-to-downtime ratio, compliance, and combinations thereof.

15. A system according to claim 1, wherein at least one of the set of monitoring devices is configured such that the set of assemblies includes a first assembly and a second assembly, wherein each of the first assembly and second assembly includes a communication link to the other one of the first and the second assemblies and is configured for removable attachment to corresponding body parts of the subject, the body parts having relative motion about a joint of the subject; and
   wherein a resilient physical link couples the first and second assemblies and allows relative motion of the first and second assemblies.

16. A system according to claim 1, wherein the ergonomic metrics are chosen from the group consisting of individual cycle time, work quality, collective process imbalances, collective process interruptions, worker motion, worker speed, and combinations thereof.

17. A system according to claim 1, wherein the processing and storing the received data to provide, in a database, performance data includes a set of steps chosen from the group consisting of: confirming tasks performed; confirming the quality of tasks performed; optimizing job rotations and breaks; analyzing worker motion data for gamification; and analyzing worker motion data for use of performance based incentive programs.

* * * * *